United States Patent [19]

Capps

[11] Patent Number: 4,621,086

[45] Date of Patent: Nov. 4, 1986

[54] METHOD OF TREATING LEUKEMIA WITH PYRAZOLO[3,4,5-kl]ACRIDINES

[75] Inventor: David B. Capps, Ann Arbor, Mich.

[73] Assignee: Warner-Lambert Company, Morris Plains, N.J.

[21] Appl. No.: 821,318

[22] Filed: Jan. 22, 1986

Related U.S. Application Data

[60] Division of Ser. No. 768,310, Aug. 22, 1985, Pat. No. 4,558,730, which is a division of Ser. No. 619,258, Jun. 15, 1984, Pat. No. 4,555,572, which is a continuation-in-part of Ser. No. 515,125, Jul. 19, 1983, abandoned.

[51] Int. Cl.$^4$ .................... A61K 31/41; C07D 471/02
[52] U.S. Cl. .................... 514/287; 514/908; 546/14; 546/64
[58] Field of Search .................... 546/64; 514/287, 408

[56] References Cited

U.S. PATENT DOCUMENTS

| | | | |
|---|---|---|---|
| 3,679,699 | 7/1972 | Oppolzer | 546/82 |
| 3,712,943 | 1/1973 | Mayer et al. | 424/84 |
| 4,139,531 | 2/1979 | Ledochowski et al. | 546/106 |

OTHER PUBLICATIONS

Nunn et al., *J.C.S., Perkin I,* 1973, pp. 2367–2703.
Oppolzer, *Tetrahedron Letters,* No. 35, pp. 3091–3094, 1970.

*Primary Examiner*—Donald G. Daus
*Assistant Examiner*—Stephen M. Kapner
*Attorney, Agent, or Firm*—Ronald A. Daignault

[57] ABSTRACT

Pyrazolo[3,4,5-kl]acridines are described as antibacterial agents and antitumor agents as well as pharmaceutical compositions and methods for their preparation.

2 Claims, No Drawings

METHOD OF TREATING LEUKEMIA WITH PYRAZOLO[3,4,5-kl]ACRIDINES

This is a division of application Ser. No. 768,310 filed Aug. 22, 1985, now U.S. Pat. No. 4,558,730, which is a division of application Ser. No. 619,258 filed June 15, 1984, now U.S. Pat. No. 4,555,572, which is in turn a continuation in part of application Ser. No. 515,125 filed July 19, 1983, now abandoned.

TECHNICAL FIELD

The invention relates to novel substituted pyrazolo[3,4,5-kl]acridines, to methods for their production, to pharmaceutical compositions comprising the compounds, and to methods of treatment using the compounds in dosage form. The compounds of the invention have pharmacological properties and are useful antimicrobial agents and antitumor agents.

BACKGROUND OF THE INVENTION

The pyrazolo[3,4,5-kl]acridine ring system is known, although not in fully aromatic form. The following reports are representative of the known literature for the pyrazolo[3,4,5-kl]acridine ring system: Tetrahedron Lett. 1970, 3091; JSC Perkin I, 1973, 2697; Chem. Ber., 109, 1898 (1976).

SUMMARY OF THE INVENTION

The invention in one aspect relates to pyrazolo[3,4,5-kl]acridine compounds having in free base form the structural formula 1 or 2:

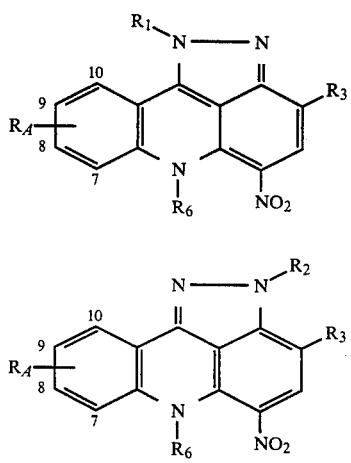

and the pharmaceutically acceptable salts thereof, where $R_1$ and $R_2$ are each alkylene-$NR_xR_y$ where alkylene is two to four carbon straight or branched chain alkylene, which can be substituted by hydroxyl, and $R_x$ and $R_y$ are each independently H, one to four carbon straight or branched chain alkyl, or two to four carbon straight or branched chain hydroxyalkyl, combined with said nitrogen represent piperidyl or pyrrolidyl, when $R_x$ and $R_y$ are both alkyl, the amine may be an N-oxide; $R_3$ is H or $NO_2$; $R_6$ is H or one to three carbon straight or branched chain alkyl; $R_A$ is H or one or two groups selected from hydroxy, chloro, amino, one to four carbon straight or branched alkylamino or dialkylamino optionally substituted by methoxy, one to four carbon straight or branched alkyl, one to six carbon straight or branched alkoxy which may be substituted by methoxy, dimethylaminoethoxy, dimethylaminopropoxy, diethylaminoethoxy, diethylaminopropoxy, benzyloxy or benzyloxy substituted by methoxy, three to ten carbon straight or branched trialkylsilyloxy, two to twelve carbon straight or branched alkanoyloxy which may be substituted by methoxy, benzoyloxy or benzoyloxy substituted by methoxy, one to four carbon straight or branched alkoxycarbonyloxy, benzyloxycarbonyloxy, one to four carbon straight or branched alkylaminocarbonyloxy or dialkylaminocarbonyloxy.

The invention in a preferred aspect relates to pyrazolo[3,4,5-kl]acridine compounds having in free base form the structural formula 1 or 2 where $R_1$ and $R_2$ are each $CH_2CH_2NHCH_2CH_2OH$, $CH_2CH_2N(C_2H_5)_2$, $CH_2CH_2N(CH_3)_2$, $CH_2CH_2NHCH_3$, $CH_2CH_2NHC_2H_5$ or $CH_2CH_2CH_2N(CH_3)_2$; $R_3$ is H or $NO_2$; $R_6$ is H or methyl; $R_A$ is as defined above or more preferably H, OH, one to six carbon straight or branched alkoxy which may be substituted by methoxy, three to ten carbon straight or branched trialkylsilyloxy, two to twelve carbon straight or branched alkanoyloxy which may be substituted by methoxy, or one to four carbon straight or branched alkoxycarbonyloxy.

The compounds of the invention form pharmaceutically acceptable salts with both organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, lactic, gluconic, glucuronic, sulfamic, benzoic, tartaric, pamoic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms with pharmaceutically acceptable solvents such as water, ethanol, and the like are equivalent to the unsolvated forms for purposes of the invention.

The compounds of formulae 1 and 2 may exist in equilibrium tautomeric forms as illustrated below:

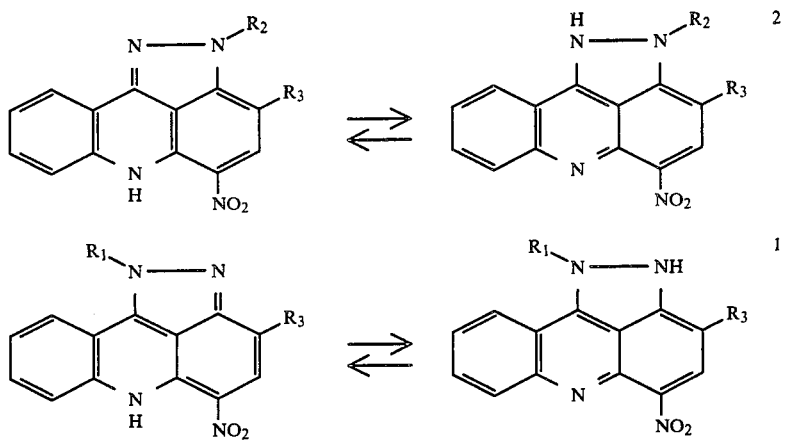

The invention in another aspect relates to compounds having in free base form the structural formula 2a

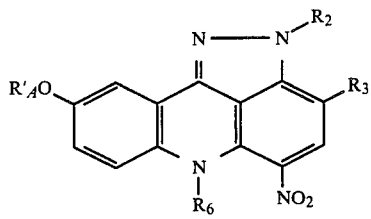

and the pharmaceutically acceptable salts thereof; wherein $R_2$, $R_3$, and $R_6$ have the above meaning and $R_A'$ is H, one to four straight or branched alkyl, benzyl, two to twelve straight or branched alkanoyl which may be substituted by methoxy three to ten carbon straight or branched trialkylsilyl or one to four straight or branched alkoxycarbonyl.

The invention in another aspect relates to compounds having the structural formulas 1 and 2, and the pharmaceutically acceptable salts thereof, that are most preferred for their pharmacological properties. These compounds in free base form, have the following names:

2-[[2-(5-nitropyrazolo[3,4,5-kl[acridin-2(6H)-yl)-ethyl-]amino]ethanol;

9-methoxy-N,N-dimethyl-5-nitropyrazolo[3,4,5-kl]-acridine-2(6H)-ethanamine;

N,N-diethyl-9-methoxy-5-nitropyrazolo-[3,4,5-kl]-acridine-2(6H)-ethanamine;

N,N-diethyl-9-methoxy-5-nitropyrazolo-[3,4,5-kl]acridine-1(6H)-ethanamine;

N,N-diethyl-5-nitropyrazolo[3,4,5-kl]acridine-2(6H)-ethanamine;

2-[2-(diethylamino)ethyl]-2,6-dihydro-5-nitropyrazolo[3,4,5-kl]acridine-9-ol;

9-ethoxy-N,N-diethyl-5-nitropyrazolo[3,4,5-kl]acridine-2(6H)-ethanamine;

9-butoxy-N,N-diethyl-5-nitropyrazolo[3,4,5-kl]acridine-2(6H)-ethanamine;

2,2-dimethylpropanoic acid 2-[2-(diethylamino)ethyl]-2,6-dihydro-5-nitropyrazolo[3,4,5-kl[acridine-9-yl ester;

9-[[(1,1-dimethylethyl)dimethylsilyl]oxy]-N,N-diethyl-5-nitropyrazolo[3,4,5-kl]acridine-2(6H)-ethanamine;

2-[2-(diethylamino)ethyl]-2,6-dihydro-5-nitropyrazolo[3,4,5-kl]acridine-9-ol acetate ester;

N,N-diethyl-5-nitro-9-propoxypyrazolo[3,4,5-kl]acridine-2(6H)-ethanamine;

carbonic acid [2-[2-(diethylamino)ethyl]-2,6-dihydro-5-nitropyrazolo[3,4,5-kl]acridine-9-yl]ethyl ester;

butanoic acid [2-[2-(diethylamino)ethyl]-2,6-dihydro-5-nitropyrazolo-[3,4,5-kl]acridine-9-yl]ester;

9-ethoxy-N,N-dimethyl-5-nitropyrazolo[3,4,5-kl]acridine-2(6H)-ethanamine;

N,N-diethyl-9-methoxy-5-nitropyrazolo[3,4,5-kl]acridine-2(6H)-propanamine;

9-methoxy-N,N-dimethyl-5-nitropyrazolo[3,4,5-kl]acridine-2(6H)-propanamine;

9-ethoxy-N,N-dimethyl-5-nitropyrazolo[3,4,5-kl]acridine-2(6H)-propanamine;

2-[3-(dimethylamino)propyl]-2,6-dihydro-5-nitropyrazolo[3,4,5-kl-]acridine-9-ol;

2-[3-(dimethylamino)propyl]-5-nitropyrazolo[3,4,5-kl]acridine-9-ol acetate ester;

2,2-dimethylpropanoic acid, [2-[3-(dimethylamino)-propyl]-2,6-dihydro-5-nitropyrazolo[3,4,5-kl]acridine-9-yl ester;

N-ethyl-9-methoxy-5-nitropyrazolo[3,4,5-kl]acridine-2(6H)-ethanamine;

9-methoxy-N,N-dimethyl-3,5-dinitropyrazolo[3,4,5-kl]acridine-2(6H)-ethanamine;

9-methoxy-N,N-dimethyl-3,5-dinitropyrazolo[3,4,5-kl]acridine-2(6H)-propanamine;

9-ethoxy-N,N-diethyl-3,5-dinitropyrazolo[3,4,5-kl]acridine-2(6H)-ethanamine;

2-[2-(diethylamino)ethyl]-2,6-dihydro-3,5-dinitropyrazolo[3,4,5-kl]acridin-9-ol;

N,N-diethyl-9-methoxy-3,5-dinitropyrazolo[3,4,5-kl]acridine-2(6H)-ethanamine;

and the pharmaceutically acceptable salts thereof.

PROCESS FOR PREPARING THE COMPOUNDS

The invention in one process aspect comprises a process for preparing compounds having the structural formula 3:

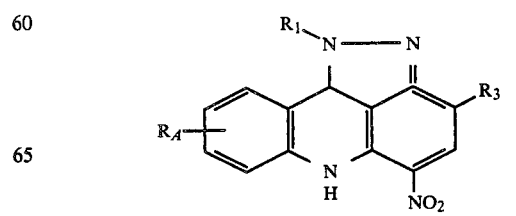

by reacting a 1,9-dichloracridine having the structural formula 4:

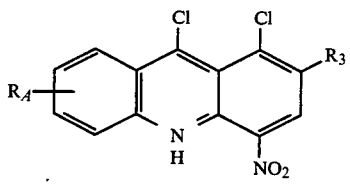

and $R_1$ substituted hydrazine having the structural formula $H_2NNHR_1$, and isolating the product in free base form or pharmaceutically acceptable salt form; where $R_1$ has the above meaning and $R_A$ is H or one or two groups selected from hydroxy, chloro, amino, one to four carbon straight or branched alkylamino or dialkylamino optionally substituted by methoxy, one to four carbon straight or branched alkyl, one to six carbon straight or branched alkoxy which may be substituted by methoxy, dimethylaminoethoxy, dimethylaminopropoxy, diethylaminoethoxy, diethylaminopropoxy, benzyloxy or benzyloxy substituted by methoxy. The reaction conditions can be varied widely. The reaction is usually carried out in a solvent at temperatures between about 0° to about 80° C. Suitable solvents are THF, THF-methanol, toluene, chlorobenzene, acetonitrile, and chloroform. When $R_3$ is nitro, compounds having structural formula 3 may also be obtained by adding two equivalents of an $R_1$-substituted hydrazine all at once to a 1-chloro-2,4-dinitroacridinone derivative at about 25° to 50° C. When the reaction ceases, the mixture is made acidic with excess strong acid.

The invention in another process aspect comprises a process for preparing compounds having the structural formula 2:

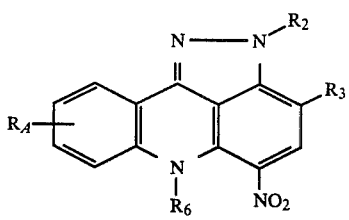

by reacting a 1-chloro-4-nitro-9(10H)-acridone having the structural formula 5:

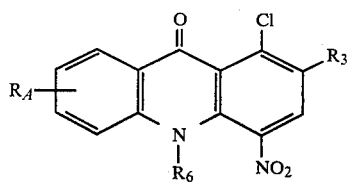

at least two equivalents of an $R_2$-substituted hydrazine having the structural formula $H_2NNHR_2$, and isolating the product in free base form or pharmaceutically acceptable salt form; where $R_2$, and $R_6$ have the above meaning and $R_A$ is H or one or two groups selected from hydroxy, chloro, amino, one to four carbon straight or branched alkylamino or dialkylamino optionally substituted by methoxy, one to four carbon straight or branched alkyl, one to six carbon straight or branched alkoxy which may be substituted by methoxy, dimethylaminoethoxy, dimethylaminopropoxy, diethylaminoethoxy, diethylaminopropoxy, benzyloxy or benzyloxy substituted by methoxy. The reaction conditions can be varied widely. The reaction is usually carried out in a solvent at temperatures between about 25° to about 130° C. Suitable solvents are toluene, tetrahydrofuran, acetonitrile, and pyridine. Acid scavengers may be employed such as $K_2CO_3$, $Et_3N$ or solvent pyridine; however, an excess of the hydrazine is preferred.

The invention in another process aspect comprises a process for preparing compounds having the structural formula 6:

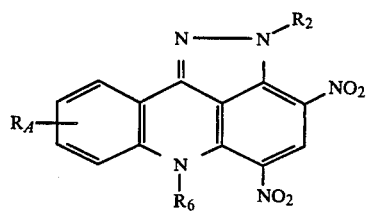

by reacting a 1-chloro-2,4-dinitro-9(10H)-acridone having the structural formula 7:

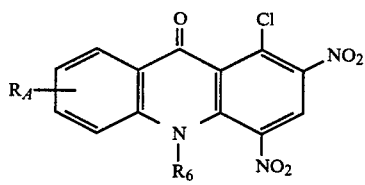

with one equivalent of an $R_2$-substituted hydrazine in the presence of a tertiary amine such as triethylamine or pyridine at temperatures between about $-20°$ to about $0°$ C. The reaction can be carried out in a solvent such as acetonitrile, pyridine, THF or THF-methanol.

The requisite hydrazines are prepared by reaction of hydrazine with the appropriate alkyl halide, $XR_1$ or $XR_2$, where $R_1$ and $R_2$ have the above meaning [J. Med. Chem., 7, 403 (1964)], or by other methods known in the art.

In another aspect, the invention concerns a process for preparing compounds having the structural formula 2 wherein $R_6$ has the above meaning; $R_3$ is H; $R_2$ is $CH_2CH_2NR_xR_y$ where $R_x$ and $R_y$ have the above meaning, and RA is H or one or two groups selected from hydroxy, chloro, amino, one to four carbon straight or branched alkylamino or dialkylamino optionally substituted by methoxy, one to four carbon straight or branched alkyl, one to six carbon straight or branched alkoxy which may be substituted by methoxy, dimethylaminoethoxy, dimethylaminopropoxy, diethylaminoethoxy, diethylaminopropoxy, benzyloxy or benzyloxy substituted by methoxy which comprises reacting a 1-chloro-4-nitro-9(10H)acridone with hydroxyethylhydrazine which product is treated with p-toluenesulfonyl chloride at about 100° C for about 30 minutes in the presence of pyridine and an appropriate solvent to afford a chloroethyl compound which chloride ion is displaced with an amino group $-NR_xR_y$ by reacting the chloroethyl compound with the appropriate amine in an autoclave at about 100° C.

Another aspect of the present invention is a process for preparing compounds of formulae 1 or 2, wherein $R_1$, $R_2$, $R_3$, and $R_6$ have the above meaning and $R_A$ is three to ten carbon straight or branched trialkylsilyloxy, two to twelve carbon straight or branched alkanoyloxy which may be substituted by methoxy, benzoyloxy or benzoyloxy substituted by methoxy, one to four carbon straight or branched alkoxycarbonyloxy, benzoyloxycarbonyloxy, one to four carbon straight or branched alkylaminocarbonyloxy or dialkylaminocarbonyloxy, in free base form or pharmaceutically acceptable salt form, which comprises reacting a compound of the formulae

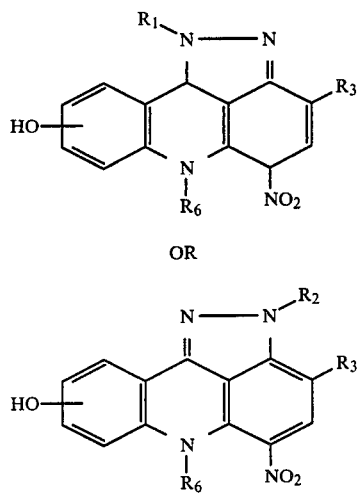

with a corresponding reactive derivative of an $R_4$-carboxylic acid, $R_4$-carbamic acid, $R_4$-carbonic acid or $R_4$-halide at room or above room temperatures in conventional solvents and in the presence of an organic base.

A reactive derivative of a carboxylic acid, carbonic acid or carbamic acid is a halide or anhydride thereof and preferably the corresponding acid chlorides.

The preferred halide is the chloride or bromide and the preferred organic base is triethylamine or diisopropylethyl amine.

The reaction is run at about 25° to 100° C. in solvents such as tetrahydrofuran (THF) or 1,2-dichloroethane.

Purification of compounds or products obtained by the methods of the invention is accomplished in any suitable way, preferably by column chromatography or crystallization.

The invention in its composition aspect relates to a pharmaceutical composition comprising a compound having structural formula 1 or a pharmaceutically acceptable salt thereof in combination with a pharmaceutically acceptable carrier.

The invention in another aspect relates to a pharmaceutical composition comprising a compound having structural formula 2 or a pharmaceutically acceptable carrier.

The invention in another method aspect relates to a method for treating microbial infection in a mammal which comprises administering a sufficient amount of a compound having structural formula 1 or a pharmaceutically acceptable salt thereof in combination with a pharmaceutically acceptable carrier, to a mammal in need thereof.

The invention in another method aspect relates to a method for treating microbial infection in a mammal which comprises administering a sufficient amount of a compound having structural formula 2 or a pharmaceutically acceptable salt thereof in combination with a pharmaceutically acceptable carrier, to a mammal in need thereof.

The invention in another method aspect relates to a method for treating leukemia in a mammal which comprises administering a sufficient amount of a compound having structural formula 1 or a pharmaceutically acceptable salt thereof in combination with a pharmaceutically acceptable carrier, to a mammal in need thereof.

The invention in another method aspect relates to a method for treating leukemia in a mammal which comprises administering a sufficient amount of a compound having structural formula 2 or a pharmaceutically acceptable salt thereof in combination with a pharmaceutically acceptable carrier, to a mammal in need thereof.

The invention in another method aspect relates to a method for treating solid tumors in a mammal which comprises administering a sufficient amount of a compound having structural formula 1 or a pharmaceutically acceptable salt thereof in combination with a pharmaceutically acceptable carrier, to a mammal in need thereof.

The invention in another method aspect relates to a method for treating solid tumors in a mammal which comprises administering a sufficient amount of a compound having structural formula 2 or a pharmaceutically acceptable salt thereof in combination with a pharmaceutically acceptable carrier, to a mammal in need thereof.

PHYSICAL AND PHARMACOLOGICAL PROPERTIES OF THE COMPOUNDS

The pyrazolo[3,4,5-kl]acridine compounds of the invention range in color from beige to orange. They are crystalline solids that are stable under normal atmospheric conditions. The compounds typically have melting points or decomposition points in the range of about 100° to about 300° C.

The compounds are useful as pharmacological agents for the treatment of bacterial infections or solid tumors in warm-blooded animals. The activity of representative compounds of the invention was established by test protocols that will now be described briefly.

Test Protocols

1. In Vitro (a) One test protocol is the in vitro proliferating human colon adenocarcinoma (HCA) cell screen. In this test, HCT-8 cells (HCA cell line received from Yale University) are trypsinized using trypsin-EDTA. A single cell suspension is achieved by passing the cells through a 26 gauge needle with a 20-cc syringe. A cell suspension is prepared using RPMI 1640+10% FCS +50 µg/ml gentamicin sulfate with a cell concentration is approximately 30,000 cells/ml. The cell suspension is dispensed in Linbro 24-well plates; 1 ml/well. The plates are incubated for approximately 48 hours at 37° C. in a 5% $CO_2$ atmosphere. At this time test compounds are added in the appropriate concentration. Five µl of the 200 µg/ml stock solution is added to each well in a primary test. Then µl of the appropriate dilution is added to each well for a titration test. The plates are reincubated an additional 60 to 65 hours at 37° C. in a 5% $CO_2$ atmosphere. The cells are lysed using a mix of cationic surfactant, glacial acetic acid, and sodium chloride. Two ml of the lysed cell suspension from each well is added to 8 ml of diluent. The number of nuclei is determined using a Coulter counter (ZBI model), and a percent growth for each drug concentration is calculated. From this, and $ID_{50}$ (molar concentration of compound that results in 50% inhibition of growth) is determined.

(b) Another test protocol is the in vitro antibacterial-/antifungal (ABF) test. Compounds are tested for antimicrobial activity in an agar-disk diffusion assay, a standard microbiological technique for testing antibiotics. After incubation of each culture with a test compound, a zone of inhibition is determined. The zone diameter (mm) of active compounds ranges from a minimum of 14 mm to as high as 60 mm, with a greater diameter reflecting higher activity. For convenience, values are reported for (*Alcaligenes viscolactis, Sarcina lutea, Branhamella catarrhalis, Bacillus subtilis,* and *Streptococcus faecalis.*

(c) Another test protocol is the PDC test. L1210 cells, a murine leukemia cell line, were grown in RPMI 1640 supplemented with 10% fetal bovine serum and genamicin (50 µg/ml). Drug dilutions were prepared in the appropriate solvent and 20 µl of each dilution were added to 24-well Linbro tissue culture plates followed by the addition of 2.0 ml of cell suspension containing $3 \times 10^4$ cells per ml. Solvent and medium controls were included in each test. After incubation at 37° C. for three days in 5% $CO_2$ in air, the contents of each well were removed and the cells counted in a ZBI Coulter counter. Percent growth was calculated relative to the controls and the levels of drug activity were expressed as $ID_{50}$ in terms of molarity (M).

(d) Still another test protocol is the in vitro antibacterial (ABMF) test which is a recognized standard microdilution susceptibility procedure in Mueller-Hinton broth against gram-positive and gram-negative bacterial test organisms. The procedure is a modification of a state-of-the-art procedure reported in *Manual of Clinical Microbiology,* Lennette, E. H., ed., by Barry, A. L. and C. Thornsberry at pages 463–474 and by Gavan, T. L. and A. L. Barry at pages 459–462, American Society for Microbiology, Washington, 1980.

In the test, a given bacterial culture is used to inoculate individual test wells of microdilution trays containing growth medium and test compound, the latter in a microdilution series: 1000, 333, 111, 37, 12, 4, 1.4, and 0.46 micrograms per milliliter. The resulting inoculated trays are each sealed, incubated with blank controls at 37° C. for 16–24 hours, and then read for minimum inhibitory concentration (MIC), the lowest concentration of test compound that completely inhibits bacterial growth. MIC values lower than 333 mcg/ml indicate antimicrobial activity. For convenience, values are reported for *Escherichia coli, Branhamella catarrhalis, Alcaligenes viscolactis, Streptococcus pneumoniae,* and *Bacillus cereus*

2. In Vivo

Another test protocol is the in vivo lymphocytic leukemia P388 test. The animals used are either male or female $CD_2F_1$ mice, six or seven animals per test group. The tumor transplant is by intraperitoneal injection of dilute ascitic fluid containing cells of lymphocytic leukemia P388. The test compounds are administered intraperitoneally once daily for five consecutive days at various doses following tumor inoculation. The animals are weighed and survivors are recorded on a regular basis for 30 days. A compound is designated "toxic" if, at a given dose, all animals died prior to four days after the first injection of drug. A ratio of survival time for treated (T)/control (C) animals is calculated. A criterion for efficacy is a ratio T/C times 100 greater than or equal to 125. See *Cancer Chemotherapy Reports,* Part 3, 3, 1 (1972) for a comprehensive discussion of the protocol.

These test protocol procedures gave results listed in the following Tables for representative compounds of the invention.

TABLE 1

Structure: Acridine-type compound with substituents N—N—R$_2$, R$_5$, R$_6$, R$_A$ at positions 7, 8, 9, 10.

| Example | R$_2$ | R$_5$ | R$_6$ | R$_A$ | Formula | mp, °C. | HCA in vitro ID$_{50}$ avg. | P388 in vivo Dose (mg/kg) | T/C × 100 | A. viscol. | S. lutea | S. catarrh. | S. subtil. | S. faecalis |
|---|---|---|---|---|---|---|---|---|---|---|---|---|---|---|
| 6 | CH$_2$CH$_2$N(Et)$_2$ | NO$_2$ | CH$_3$ | 9-OCH$_3$ | C$_{21}$H$_{25}$N$_5$O$_3$·CH$_3$SO$_3$H | 190–190° | 3.1 × 10$^{-7}$ | 50.00 / 25 / 12.5 | 230 / 173 / 151 | 15 (.1) | 15 (.5) | 16 (.5) | 19 (.5) | 15 (1) |
| 5 | CH$_2$CH$_2$N(Et)$_2$ | NO$_2$ | H | 9-OCH$_3$ | C$_{20}$H$_{23}$N$_5$O$_3$·CH$_3$SO$_3$H | 228–231° dec. | 1.2 × 10$^{-7}$ | 25 / 12.5 / 6.25 / 50 / 25 / 12.5 | 142 / 228 / 187 / 148 / 242 / 197 | 18 (.1) | 14 (.5) | 16 (.1) | 15 (.1) | 14 (1) |
| 2 | CH$_2$CH$_2$N(Et)$_2$ | NO$_2$ | CH$_3$ | H | C$_{20}$H$_{23}$N$_5$O$_2$·CH$_3$SO$_3$H | 188–189° | 1.0 × 10$^{-6}$ | 25.00 / 12.50 / 6.25 / 3.12 | 158 / 143 / 184 / 126 | 20 (.1) | 19 (.5) | 17 (.1) | 18 (.1) | 16 (.5) |
| 1 | CH$_2$CH$_2$N(Et)$_2$ | NO$_2$ | H | H | C$_{19}$H$_{21}$N$_5$O$_2$·CH$_3$SO$_3$H | 239–241° dec. | 3.0 × 10$^{-7}$ | 25.00 / 12.50 / 6.25 / 5.00 / 2.50 | 165 / 163 / 122 | 22 (.1) | 14 (.1) | 17 (.1) | 15 (.5) | 17 (.5) |
| 5a | CH$_2$CH$_2$N(Me)$_2$ | NO$_2$ | H | 9-OCH$_3$ | C$_{18}$H$_{19}$N$_5$O$_3$·CH$_3$SO$_3$H·½H$_2$O | 237–240° | 1.0 × 10$^{-7}$ | 50.00 / 25.00 / 12.50 | 275 / 228 / 181 | 19 (.1) | 16 (1) | 21 (.5) | 14 (.1) | 15 (.5) |
| 4 | H, CH$_2$CH$_2$NCH$_2$CH$_2$OH | NO$_2$ | H | H | C$_{18}$H$_{19}$N$_5$O$_3$·CH$_3$SO$_3$H | 178–179° | 6.8 × 10$^{-7}$ | 50.00 / 25.00 / 50.00 / 25.00 | 180 / 120 / 160 / 131 | 19 (.1) | 19 (.5) | 16 (.1) | 20 (.1) | 18 (.5) |
| 3 | H, CH$_2$CH$_2$NCH$_2$CH$_2$OH | NO$_2$ | H | H | C$_{17}$H$_{17}$N$_5$O$_3$·HCl | >300° | 1.5 × 10$^{-7}$ | 25.00 / 12.50 / 6.25 / 3.12 | 185 / 158 / 132 / 122 | 21 (.1) | 14 (.5) | 25 (.5) | 18 (.1) | 15 (.5) |
| 7 | H, CH$_2$CH$_2$NCH$_2$CH$_2$OH | NO$_2$ | H | 9-OCH$_3$ | C$_{18}$H$_{19}$N$_5$O$_4$·HCl | >315° dec. | 1.9 × 10$^{-7}$ | 50.00 / 25.00 / 12.50 / 6.25 | 163 / 149 / 138 / 138 | | 14 (1) | 14 (.1) | 18 (.5) | 14 (1) |
| 10 | CH$_2$CH$_2$N(Et)$_2$ | NO$_2$ | H | 9-OH | C$_{19}$H$_{21}$N$_5$O$_3$ | 241–244° dec. | 1.3 × 10$^{-8}$ | 3.00 / 1.50 / 0.75 / 0.38 | 180 / 158 / 149 / 138 | 15 (.01) | 14 (1) | 18 (.1) | 17 (.1) | 16 (.5) |
| 11 | CH$_2$CH$_2$N(Et)$_2$ | NO$_2$ | H | 9-C$_7$H$_7$ | C$_{26}$H$_{22}$N$_5$O$_3$·CH$_3$SO$_3$H | 216–218° dec. | 2.3 × 10$^{-6}$ | 50.00 / 25.00 / 12.50 | 194 / 141 / 127 | | | | | |

ABF zone diameter (Dose in mg/ml)

TABLE 2
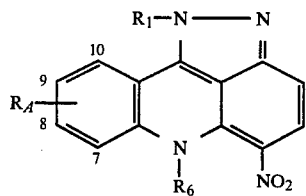
| Example | $R_2$ | $R_5$ | $R_6$ | $R_A$ | Formula | mp, °C. | HCA in vitro $ID_{50}$ avg. | P388 in vivo Dose (mg/kg) | T/C × 100 | ABF zone diameter (Dose in mg/ml) | | | | |
|---|---|---|---|---|---|---|---|---|---|---|---|---|---|---|
| | | | | | | | | | | A. viscol | S. lutea | B. catarrh. | B. subtil. | S. faecalis |
| 8 | $CH_2CH_2N(Et)_2$ | $NO_2$ | H | H | $C_{19}H_{21}N_5O_2$ · $CH_3SO_3H$ | 204–206° | $9.3 \times 10^{-8}$ | 25.00 | 186 | 23 (.1) | 18 (.5) | 15 (.01) | 0 (3) | 18 (.5) |
| | | | | | | | | 12.50 | 140 | | | | | |
| | | | | | | | | 50.00 | 211 | | | | | |
| | | | | | | | | 25.00 | 165 | | | | | |
| 9 | $CH_2CH_2N(Et)_2$ | $NO_2$ | H | 9-$OCH_3$ | $C_{20}H_{23}N_5O_3$ · $CH_3SO_3H$ | 265–270° dec. | $1.0 \times 10^{-7}$ | 50.00 | 167 | | 14 (.1) | 16 (.1) | 15 (.1) | 18 (.5) |
| | | | | | | | | 25.00 | 135 | | | | | |
| | | | | | | | | 12.50 | 120 | | | | | |
| | | | | | | | | 50.00 | 177 | | | | | |
| | | | | | | | | 25.00 | 138 | | | | | |

TABLE 3

$$\text{Structure: tricyclic acridine with } R_A \text{ at 7,8,9,10 positions and } N-N-R_2 \text{ substituent, } NO_2 \text{ group}$$

| Example | R$_2$ | R$_A$ | Formula | mp °C. | HCA ID$_{50}$ Avg. (M) | PDC ID$_{50}$ (M) | P388 in Vivo Dose (mg/kg) | T/C × 100 | ABMF Test M.I.C. (μg/ml) E. coli | A. visc. | B. cata. | S. pneu. | B. cere. |
|---|---|---|---|---|---|---|---|---|---|---|---|---|---|
| 17 | CH$_2$CH$_2$N(Et)$_2$ | 7-OCH$_3$ | C$_{20}$H$_{23}$N$_5$O$_3$·CH$_3$SO$_3$H | 195-198 | 5.1 × 10$^{-7}$ | 6.4 × 10$^{-7}$ | 12.5 | 106 | <0.46 | <0.46 | <0.46 | <0.46 | <0.46 |
| 18 | CH$_2$CH$_2$N(Et)$_2$ | 9-OC$_2$H$_5$ | C$_{21}$H$_{25}$N$_5$O$_3$·2CH$_3$SO$_3$H | 212-214 | 1.1 × 10$^{-7}$ | 7.9 × 10$^{-7}$ | 12.5 6.25 3.13 | 201 220 169 135 | 12.3 | <0.46 | 1.4 | <0.46 | 12.3 |
| 19 | CH$_2$CH$_2$N(Et)$_2$ | 9-OCH$_2$CH$_2$CH$_3$ | C$_{22}$H$_{27}$N$_5$O$_3$·CH$_3$SO$_3$H | 209-210 | 3.1 × 10$^{-7}$ | 4.6 × 10$^{-7}$ | 12.5 6.25 3.12 | 222 167 137 | >1000 | <0.46 | <0.46 | <0.46 | 12.3 |
| 20 | CH$_2$CH$_2$N(Et)$_2$ | 9-O(CH$_2$)$_3$CH$_3$ | C$_{23}$H$_{29}$N$_5$O$_3$·CH$_3$SO$_3$H | 187-189 | 7.3 × 10$^{-8}$ | 1.2 × 10$^{-6}$ | 12.5 6.25 3.12 1.56 | 146 209 160 125 124 | | | | | |
| 21 | CH$_2$CH$_2$N(Et)$_2$ | 9-OCH$_2$CH$_2$NEt$_2$ | C$_{25}$H$_{34}$N$_6$O$_3$·2CH$_3$SO$_3$H | 212-214 | | 4.6 × 10$^{-7}$ | | | 111 | 4.1 | 12.3 | 12.3 | 37 |
| 22 | CH$_2$CH$_2$N(Et)$_2$ | 9-OC$_7$H$_6$—p-OCH$_3$ | C$_{27}$H$_{29}$N$_5$O$_4$·CH$_3$SO$_3$H | 182-183 | | 8.2 × 10$^{-7}$ | | | | | | | |
| 23 | CH$_2$CH$_2$N(Et)$_2$ | 7,9-di(OCH$_3$) | C$_{21}$H$_{25}$N$_5$O$_4$·CH$_3$SO$_3$H·H$_2$O | 241-242 | 4.9 × 10$^{-7}$ | 7.6 × 10$^{-7}$ | | | 37 | <0.46 | 1.4 | <0.46 | <0.46 |
| 24 | CH$_2$CH$_2$N(Et)$_2$ | 8,10-di(OCH$_3$) | C$_{21}$H$_{25}$N$_5$O$_4$·CH$_3$SO$_3$H·H$_2$O | 240-241 | | 4.9 × 10$^{-7}$ | | | 4.1 | <0.46 | <0.46 | 1.4 | <0.46 |
| 25 | CH$_2$CH$_2$N(Et)$_2$ | 9-OCH$_3$ 10-Cl | C$_{20}$H$_{22}$ClN$_5$O$_3$·CH$_3$SO$_3$H·H$_2$O | 271-273 | | 7.0 × 10$^{-8}$ | | | <0.46 | <0.46 | <0.46 | <0.46 | <0.46 |
| 26 | CH$_2$CH$_2$N(Et)$_2$ | 9-OSiMe$_2$CMe$_3$ | C$_{25}$H$_{35}$N$_5$O$_3$Si·CH$_3$SO$_3$H | 207-213 | 6.4 × 10$^{-9}$ | 1.7 × 10$^{-7}$ | | | >1000 | 37 | >1000 | >1000 | >1000 |
| 27 | CH$_2$CH$_2$N(Et)$_2$ | 9-OAc | C$_{21}$H$_{23}$N$_5$O$_4$·CH$_3$SO$_3$H | 249-251 (dec.) | 5.3 × 10$^{-9}$ | 3.8 × 10$^{-9}$ | 6.25 3.12 1.56 | 211 158 154 | 12.3 | 0.46 | 0.46 | 1.4 | 4.1 |
| 28 | CH$_2$CH$_2$N(Et)$_2$ | 9-OCO(t-Bu) | C$_{24}$H$_{29}$N$_5$O$_4$·CH$_3$SO$_3$H | 233-235 | 9.7 × 10$^{-9}$ | 7.2 × 10$^{-9}$ | 6.25 3.12 1.56 | 165 218 158 | | | | | |
| 29 | CH$_2$CH$_2$N(Et)$_2$ | 9-OCOCH$_2$CH$_2$CH$_3$ | C$_{23}$H$_{27}$N$_5$O$_4$·CH$_3$SO$_3$H | 220-222 | | 4.3 × 10$^{-9}$ | 6.25 3.12 | 223 221 | 333 | <0.46 | 1.4 | <0.46 | 4.1 |
| 30 | CH$_2$CH$_2$N(Et)$_2$ | 9-OCO(CH$_2$)$_6$CH$_3$ | C$_{27}$H$_{35}$N$_5$O$_4$·CH$_3$SO$_3$H·0.5 H$_2$O | 159-163 | | 4.3 × 10$^{-9}$ | 6.25 | 252 | 37 | <0.46 | 12.3 | <0.46 | 37 |

TABLE 3-continued $$\text{N} - \text{N} - \text{R}_2$$

(structure: tricyclic acridine-like system with R_A at positions 8,9,10 and NO_2 at position 7, N-H)

| Example | R₂ | R_A | Formula | mp °C. | HCA ID₅₀ Avg. | PDC ID₅₀ (M) | Dose (mg/kg) | P388 in Vivo T/C × 100 | E. coli | A. visc. | B. cata. | S. pneu. | B. cere. |
|---|---|---|---|---|---|---|---|---|---|---|---|---|---|
| 31 | CH₂CH₂N(Et)₂ | 9-OCOC₆H₅ | C₂₆H₂₅N₅O₄·CH₃SO₃H·H₂O | 225-228 | | $3.0 \times 10^{-9}$ | 6.25 | 168 | | | | | |
| 32 | CH₂CH₂N(Et)₂ | 9-OCO₂C₂H₅ | C₂₂H₂₅N₅O₅·CH₃SO₃H | 199-201 | | $3.2 \times 10^{-9}$ | 3.12 | 208 | 4.1 | <0.46 | 1.4 | <0.46 | <0.46 |
| 33 | CH₂CH₂N(Et)₂ | 9-N(CH₃)₂ | C₂₁H₂₆N₆O₂·2CH₃SO₃H | 206-208 | $3.2 \times 10^{-7}$ | $9.0 \times 10^{-7}$ | 25 12.5 25 12.5 | 158 127 178 142 | 37 | 1.4 | 12.3 | 1.4 | 37 |
| 34 | CH₂CH₂N(Et)₂ | 9-CH₃ | C₂₀H₂₃N₅O₂·CH₃SO₃H | 204-207 | $7.9 \times 10^{-7}$ | $8.6 \times 10^{-7}$ | | | 12.3 | <0.46 | <0.46 | <0.46 | <0.46 |
| 35 | CH₂CH₂N(Et)₂ | H | C₁₉H₂₁N₅O₃·1.2 CH₃SO₃H·0.75 H₂O | 173-180 (dec.) | | | 12.5 6.25 | 167 128 | 12.3 | 4.1 | 12.3 | 12.3 | >1000 |
| 36 | H, CH₂CH₂NEt → O | 9-OCH₃ | C₁₈H₁₉N₅O₃·1.25CH₃SO₃H·0.5 H₂O | 228-230 | $1.2 \times 10^{-7}$ | $2.1 \times 10^{-7}$ | 50 25 12.5 | 223 160 169 | 1.4 | <0.46 | <0.46 | <0.46 | 1.4 |
| 37 | CH₂CH₂N(Me)₂ | 9-OC₂H₅ | C₁₉H₂₁N₅O₃·1.25CH₃SO₃H | 214-216 | $2.5 \times 10^{-8}$ | $2.7 \times 10^{-7}$ | 12.5 6.25 3.12 | 234 191 150 | <0.46 | <0.46 | 1.4 | <0.46 | 4.1 |
| 38 | CH₂CH₂N(Me)₂ | 7,9-di(OCH₃) | C₁₉H₂₁N₅O₃·CH₃SO₃H | 260-262 | $6.4 \times 10^{-8}$ | $2.1 \times 10^{-7}$ | 200 100 | 128 119 | 1000 | <0.46 | 1.4 | <0.46 | <0.46 |
| 39 | CH₂CH₂N(Me)₂ | 9-N(CH₃)₂ | C₁₉H₂₂N₆O₂·2CH₃SO₃H·2H₂O | 200-206 (dec.) | $1.6 \times 10^{-7}$ | $6.0 \times 10^{-7}$ | 25 12.5 6.25 | 189 164 126 | 12.3 | 1.4 | 12.3 | 1.4 | 12.3 |
| 40 | H, CH₂CH₂NCH₂CH₂OH | 9-OC₂H₅ | C₁₉H₂₁N₅O₄·HCl·0.25 H₂O | 283-285 (dec.) | $8.2 \times 10^{-8}$ | $3.2 \times 10^{-7}$ | 50 25 12.5 6.25 | 195 169 156 134 | 4.1 | <0.46 | 1.4 | <0.46 | <0.46 |

TABLE 3-continued

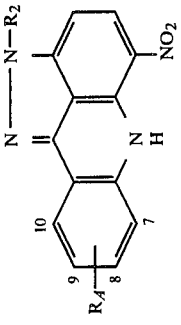

| Example | R₂ | R_A | mp °C. | Formula | HCA ID$_{50}$ Avg. | PDC ID$_{50}$ (M) | P388 in Vivo Dose (mg/kg) | P388 in Vivo T/C × 100 | ABMF Test M.I.C. (µg/ml) E. coli | A. visc. | B. cata. | S. pneu. | B. cere. |
|---|---|---|---|---|---|---|---|---|---|---|---|---|---|
| 41 | H—CH₂CH₂NCH₂CH₂OH | 9-O(CH₂)₃CH₃ | 239–241 | C₂₁H₂₅N₅O₄·CH₃SO₃H·0.5 H₂O | 3.4 × 10⁻⁷ | 6.5 × 10⁻⁷ | 12.5 / 6.25 / 3.12 / 1.56 | 174 / 159 / 147 / 141 | 3.7 | <0.46 | 1.4 | 12.3 | 12.3 |
| 42 | H—CH₂CH₂NCH₂CH₂OH | 9-CH₃ | >300 | C₁₈H₁₉N₅O₃·HCl | 2.5 × 10⁻⁷ | 5.9 10⁻⁷ | | | <0.46 | <0.46 | <0.46 | <0.46 | <0.46 |
| 43 | CH₂CH₂CH₂N(Et)₂ | 9-OCH₃ | 191–193 | C₂₁H₂₅N₅O₃·CH₃SO₃H·H₂O | 7.6 × 10⁻⁷ | 1.3 × 10⁻⁶ | 25 / 12.5 / 50 / 25 / 12.5 / 6.25 | 210 / 184 / 202 / 176 / 167 / 165 | 1.4 | <0.46 | 4.1 | <0.46 | 4.1 |
| 44 | CH₂CH₂CH₂N(Me)₂ | 9-OH | 259–261 | C₁₈H₁₉N₅O₃·CH₃SO₃H·H₂O | 1.2 × 10⁻⁸ | 1.7 × 10⁻⁹ | 3.12 / 1.56 / 0.78 / 0.39 | 270 / 200 / 182 / 162 | <0.46 | <0.46 | <0.46 | 0.46 | 0.46 |
| 45 | CH₂CH₂CH₂N(Me)₂ | 9-OCH₃ | 229–232 | C₁₉H₂₁N₅O₃·CH₃SO₃H | 1.4 × 10⁻⁷ | 4.2 × 10⁻⁷ | 25 / 12.5 / 6.25 | 261 / 227 / 189 | 12.3 | <0.46 | 1.4 | <0.46 | 1.4 |
| 46 | CH₂CH₂CH₂N(Me)₂ | 9-OC₂H₅ | 266–268 | C₂₀H₂₃N₅O₃·CH₃SO₃H | 5.5 × 10⁻⁸ | 2.2 × 10⁻⁷ | 12.5 / 6.25 / 3.12 / 1.56 | 232 / 169 / 137 / 132 | 12.3 | <0.46 | 1.4 | 4.1 | 4.1 |
| 47 | CH₂CH₂CH₂N(Me)₂ | 9-OAc | 260–264 | C₂₀H₂₁N₅O₄·CH₃SO₃H | 1.1 × 10⁻⁸ | 1.9 × 10⁻⁹ | 1.56 / 0.78 / 0.39 | 232 / 207 / 178 / 144 | <0.46 | <0.46 | <0.46 | <0.46 | <0.46 |
| 48 | CH₂CH₂CH₂N(Me)₂ | 9-OCO(t-Bu) | 243–245 | C₂₃H₂₇N₅O₄·CH₃SO₃H | | 9.8 × 10⁻⁹ | 1.56 / 0.78 | 263 / 175 | 3.7 | 0.46 | 1.4 | 4.1 | 333 |

TABLE 4

[Structure: anthracene-based compound with R₄ at position 9, =N—N—R₂ substituent, and two NO₂ groups on terminal phenyl ring]

| Example | R₂ | R₄ | Formula | mp °C. | HCA ID₅₀ Avg. | PDC ID₅₀ (M) | P388 in Vivo Dose (mg/kg) | P388 in Vivo T/C × 100 | ABMF Test M.I.C. (μg/ml) E. coli | A. visc. | B. cata. | S. pneu. | B. cere. |
|---|---|---|---|---|---|---|---|---|---|---|---|---|---|
| 49 | CH₂CH₂N(Et)₂ | 9-OH | C₁₉H₂₀N₆O₅·CH₃SO₃H·0.5 H₂O | 249-253 | | 6.8 × 10⁻⁹ | | | <0.46 | <0.46 | <0.46 | <0.46 | <0.46 |
| 50 | CH₂CH₂N(Et)₂ | 9-OCH₃ | C₂₀H₂₂N₆O₅·CH₃SO₃H·H₂O | 277-278 | 6.6 × 10⁻⁸ | 4.0 × 10⁻⁷ | 50, 25, 12.5, 6.25 | 226, 169, 166, 160 | <0.46 | <0.46 | <0.46 | <0.46 | 4.1 |
| 51 | CH₂CH₂N(Et)₂ | 9-OC₂H₅ | C₂₁H₂₄N₆O₅·CH₃SO₃H·H₂O | 278-280 | | 3.8 × 10⁻⁷ | | | >1000 | <0.46 | 333 | 111 | 333 |
| 52 | CH₂CH₂N(Et)₂ | 9-OC₇H₇ | C₂₆H₂₆N₆O₅·CH₃SO₃H·0.5 H₂O | 251-253 | | 7.5 × 10⁻⁷ | | | | | | | |
| 53 | CH₂CH₂N(Et)₂ | 9-OC₇H₆—p-OMe | C₂₇H₂₈N₆O₆·CH₃SO₃H | 218-219 (dec.) | | 6.8 × 10⁻⁹ | | | <0.46 | <0.46 | <0.46 | <0.46 | <0.46 |
| 54 | CH₂CH₂N(Me)₂ | 9-OCH₃ | C₁₈H₁₈N₆O₅·CH₃SO₃H·H₂O | 281-282 | 5.5 × 10⁻⁸ | 2.2 × 10⁻⁷ | 12.5, 12.5, 6.25, 3.12, 1.56 | 236, 232, 169, 137, 132 | 0.46 | 0.46 | 0.46 | 0.46 | 0.46 |
| 55 | CH₂CH₂CH₂N(Me₂) | 9-OCH₃ | C₁₉H₂₀N₆O₅·CH₃SO₃H | | | 2.2 × 10⁻⁷ | | | <0.46 | <0.46 | <0.46 | <0.46 | <0.46 |

TABLE 5

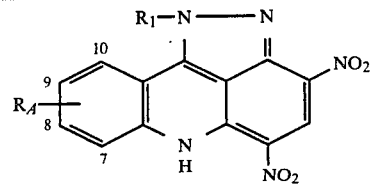

| Example | $R_1$ | $R_A$ | Formula | mp °C. | HCA $ID_{50}$ Avg. | PDC $ID_{50}$ (M) | P388 In Vivo Dose (mg/kg) | T/C × 100 | ABMF Test M.I.C. (μg/ml) E. coli | A. visc. | B. cata. | S. pneu. | B. cere. |
|---|---|---|---|---|---|---|---|---|---|---|---|---|---|
| 56 | $CH_2CH_2N(Et)_2$ | 9-$OCH_3$ | $C_{20}H_{22}N_6O_5 \cdot CH_3SO_3H$ | 285–286 (dec.) | | $1.9 \times 10^{-7}$ | | | 1000 | <0.46 | 37 | 12.3 | 333 |

PREPARATION OF PHARMACEUTICAL COMPOSITIONS

When being utilized as antimicrobial and antitumor agents, the compounds of the invention can be prepared and administered in a wide variety of topical, oral, and parenteral dosage forms. It will be clear to those skilled in the art that the following dosage forms may comprise as the active components, one or more compounds of formula 1, a corresponding pharmaceutically acceptable salt of any of said compounds, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" in intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Topical preparations include creams, lotions, gels, and sprays. These various topical preparations may be formulated by well-known procedures. See for example Remington's Pharmaceutical Sciences, Chapter 43, 14th Ed., Mack Publishing Co., Easton, Pennsylvania 18042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 50 mg to 500 mg according to the particular application and the potency of the active ingredient.

In therapeutic use as antimicrobial and antitumor agents the compounds utilized in the pharmaceutical method of this invention are administered at the initial dosage of about 0.1 mg to about 50 mg per kilogram. A dose range of about 0.5 mg to about 10 mg per kilogram is preferred. The dosages, however, may be varied depending upon the requirements of patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils.

Under ordinary conditions of storage and use, these preparations contain preservative to prevent the growth of microorganisms.

The pharmaceutical forms suitable for injectable use include sterile aqueous solutions or dispersions and sterile powders for the extemporaneous preparation of sterile injectable solutions or dispersions. In drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage from for ease of administration and uniformity of dosage. Unit dosage forms used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel unit dosage forms of the invention are dictated by and directly dependent on (a) the unique characteristics of the active material and the particular therapeutic effect to be achieved, and (b) the limitation inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in unit dosage form as hereinbefore disclosed. A unit dosage from can, for example, contain the principal active compound in amounts ranging from about 0.1 to about 500 mg, with from about 0.5 to about 250 mg being preferred. Expressed in proportions, the active compound is generally present in from about 0.1 to about 500 mg/ml of carrier. In the case of compositions containing supplementary active ingredients, the dosages are determined by reference to the usual dose and the manner of administration of the said ingredients. The daily parenteral doses for mammalian subjects to the treated ranges from 0.1 mg/kg. The preferred daily dosage range is 0.3 mg/kg to 10 mg/kg.

PREPARATIVE EXAMPLES

The invention and the best mode of practicing the same are illustrated by the following examples of preferred embodiments of selected compounds and their preparation. Temperature data are given in degrees Celsius.

EXAMPLE 1

N,N-Diethyl-5-nitropyrazolo[3,4,5-kl]acridine-2(6H)-ethanamine, methanesulfonate (1:1)

A suspension of 13.74 g (0.05 mol) of 1-chloro-4-nitro-9(10H)acridinone in 180 ml of THF, 180 ml of methanol, and 15.0 g (0.115 mol) of [2-(diethylamino)ethyl]hydrazine was stirred at room temperature for two hours and at 45 degrees for two hours. The mixture was cooled, the orange solid collected, washed with THF-methanol, acetonitrile, and dried to 13.0 g (74%), mp 185-187 degrees.

A water-soluble salt was prepared from 0.08 g of the free base and one equivalent of methanesulfonic acid in methanol-ether, mp 239-241 degrees (decomp.).

EXAMPLE 2

N,N-Diethyl-6-methyl-5-nitropyrazolo[3,4,5-kl]acridine-2(6H)-ethanamine, methanesulfonate A mixture of 4.1 g (0.014 mol) of 1-chloro-10-methyl-4-nitro-9(10H)-acridinone, 50 ml of methanol, 50 ml of THF and 4.0 g (0.03 mol) of [2-(diethylamino)ethyl)]hydrazine was stirred at room temperature for 20 hours. The resulting solution was evaporated to dryness, the residue triturated in 200 ml of water, filtered, and the precipitate recrystallized from 125 ml of ethanol, provided 4.5 g (87%) of the title free base, orange needles, mp 148-150 degrees.

The methanesulfonate (1:1) salt is obtained by dissolving the base in methanol containing an equivalent of methanesulfonic acid, and adding diethyl ether, mp 185-188 degrees.

EXAMPLE 3

2-[[2-(5-Nitropyrazolo[3,4,5-kl[acridin-2(6H)-ylethyl]amino]ethanol, monohydrochloride A suspension of 1.37 g (0.005 mol) of 1-chloro-4-nitro-9(10H)-acridinone, 0.70 g (0.0059 mol) of 2-[(hydrazinoethyl)amino]ethanol, 25 ml of THF and 25 ml of methanol was stirred under gentle reflux for 16 hours. The orange solid was collected, resuspended in 50 ml of THF and collected, resuspended in 50 ml of acetone, collected, and dried to 1.42 g (77%) of the title compound, mp above 300 degrees.

EXAMPLE 4

2-[[2-[6-Methyl-5-nitropyrazolo[3,4,5-kl-acridin-2-(6H)-yl]ethyl]amino]ethanol, methanesulfonate A warm solution of 0.87 g (0.003 mol) of 1-chloro-10-methyl-4-nitro-9(10H)-acridinone in 10 ml of THF was added to a stirred mixture of 0.83 g (0.007 mol) of 2-[(hydrazinoethyl)amino]ethanol and 50 ml of THF, and the resulting mixture stirred 18 hours at 25 degrees. The orange solid was collected, washed with methanol, and dried to 0.95 g. Nine-tenths of a gram of this free base was dissolved in 5 ml of methanol and treated with 5 ml of 1N methanesulfonic acid in methanol. The orange precipitate was redrystallized from 25 ml of chloroform-methanol and 50 ml of ethyl acetate providing 0.98 g (77%) of the title compound, mp 177-178 degrees.

EXAMPLE 5

N,N-Diethyl-9-methoxy-5-nitropyrazolo-[3,4,5-kl]acridine-2(6H)-ethanamine, methanesulfonate (1:1)

The 4.57 g (0.015 mol) of 1-chloro-7-methoxy-4-nitro-9(10H)acridinone suspended in 75 ml of THF and 75 ml of methanol was added 4.00 g (0.031 mol) of [2-(diethylamino)ethyl]hydrazine, and the suspension stirred 6 hours at 25 degrees. The orange solid was collected, washed with THF-methanol (1:), and dried to 4.55 g (79%) of the title compound free base, mp 183-185 degrees. A 1.14 g portion was converted to the methanesulfonate salt in methanol containing 0.35 g of methanesulfonic acid and a few drops of water, mp 228-231 degrees (decomp.).

In a like manner using [2-(dimethylamino)ethyl]hydrazine, there is obtained 9-methoxy-N,N-dimethyl-5- nitropyrazolo[3,4,5-kl]acridine-2(6H)-ethanamine, methanesulfonate, 5a, (1:1), mp 237-40 degrees.

EXAMPLE 6

N,N-Diethyl-9-methoxy-6-methyl-5-nitropyrazolo[3,4,5-kl]acridine-2(6H)-ethanamine, monomethanesulfonate To a stirred mixture of 0.96 g (0.003 mol) of 1-chloro-7-methoxy-10-methyl-4-nitro-9(10H)-acridinone in 25 ml of THF and 25 ml of methanol was added 0.86 g (0.0066 mol) of [2-(diechylamino)ethyl]hydrazine. After stirring the mixture 4.5 hours at 25 degrees followed by 2.5 hours at 50 degrees, the volatiles were removed by evaporation, providing a residue which was washed with water and chromatographed over 50 g of silica gel in chloroform-methanol (50:1 vol). The main fraction was evaporated to a red oil (0.03 g) which was converted to the title compound, mp 190°-193° C. by crystallization from methanol/ether containing 0.24 g of methanesulfonic acid.

EXAMPLE 7

2-[[2-(9-Methoxy-5-nitropyrazolo[3,4,5-kl]-acridin-2(6H)yl)ethyl]aminoethanol, monohydrochloride To a suspension of 3.14 g (0.0103 mol) of 1-chloro-7-methoxy-4-nitro-9(10H)-acridinone in 40 ml of THF at 25 degrees was added 1.47 g (0.0124 mol) of 2-[hydrazinoethyl)amino]ethanol in 20 ml of methanol, and the mixture stirred for three hours. The orange solid was collected and washed by trituration in THF, DMF, and acetone, successively, and dried to 2.8 g (67%) of product, mp above 315 degrees, with darkening above 285 degrees.

EXAMPLE 8

N,N-Diethyl-5-nitropyrazolo[3,4,5-kl]acridine1(6H)-ethanamine, monomethanesulfonate A mixture of 3.0 of 1-chloro-4-nitro-9(10H)acridinone, 12 ml of chlorobenzene, and 12 ml of phosphorus oxychloride is stirred and boiled under reflux for 7.5 hours. Cyclohexane (24 ml) and chlorobenzene (7 ml) are added and the mixture is boiled and evaporated until homogeneous, then allowed to cool. The precipitate of 1,9-dichloro-4-nitroacridine is collected and used immediately.

The entire precipitate from the above reaction is added to a solution of 8.2 g of [2-(diethylamino)ethyl]hydrazine in 100 ml of THF, and the mixture is stirred at room temperature for two hours. The orange precipitate is collected. The filtrate is evaporated to dryness, the residue triturated with water, and the orange solid collected. Both crops are the free base of the title compound, mp 204-206 degrees from ethanol. The 1:1 salt with methanesulfonic acid is crystallized from methanol-ether, mp 237-245 degrees with decomposition.

EXAMPLE 9

N,N-Diethyl-9-methoxy-5-nitropyrazolo[3,4,5-kl]acridine-1(6H)-ethanamine, monomethanesulfonate A suspension of 0.98 g of 1,9-dichloro-7-methoxy-4-nitroacridine and 1.31 g of [2-(diethylamino)ethyl]hydrazine in 15 ml each of THF and methanol is stirred and heated at 50 degrees for 41 hours. The yellow solid is collected and washed with methanol, then with THF, and recrystallized from acetonitrile-chloroform, providing the free base of the title compound, mp 214-216 degrees. The title compound is prepared in aqueous methanol containing an equivalent of methanesulfonic acid, as a yellow solid, melting with gaseous decomposition at 265-270 degrees.

EXAMPLE 10

2-[2-(Diethylamino)ethyl]-2,6-dihydro-5-nitropyrazolo[3,4,5,kl]acridin-9-ol, monomethanesulfonate A mixture of 1.16 g of 1-chloro-7-hydroxy-4-nitro-9(10H)-acridinone, 20 ml of THF, 20 ml of methanol, and 1.31 g of [2-(diethylamino)ethyl]hydrazine is stirred at 25 degrees for 5.5 hours, and at 40-50 degrees for 18 hours. The precipitate is suspended in 16 ml of hot methanol containing 0.3 g of methanesulfonic acid, and water is added until solution occurs. The title compound precipitates from the mixture upon cooling as dark orange crystals, mp 241-244 degrees with decomposition.

EXAMPLE 11

N,N-Diethyl-5-nitro-9-(phenylmethoxy)pyrazolo[3,4,5-kl]acridine-1(6H)-ethanamine, monomethanesulfonate A mixture of 3.26 g of 1-chloro-4-nitro-7-phenylmethoxy)-9(10H)-acridinone and 2.45 g of [2-(diethylamino)ethyl]hydrazine in 50 ml each of THF and methanol is stirred at room temperature for 18 hours. The orange precipitate is collected and recrystallized from toluene, and from chloroformcyclohexane, providing the free base of the title compound, mp 161-164 degrees. The title salt is obtained by crystallization from methanol-ethyl acetate-diethyl ether containing one equivalent of methanesulfonic acid, and recrystallized from chloroform-methanol as deep orange crystals, mp 216-218 degrees.

EXAMPLE 12

6-Chloro-2-[(4-methoxyphenyl)amino]-3-nitrobenzoic acid

To 74 g (0.60 mol) of p-anisidine, stirred mechanically at 75 degrees, was added 35.4 g (0.15 mol) of 2,6-dichloro-3-nitrobenzoic acid [Lehmstedt and Schrader, Berichte 70B, 1526 (1937)] in small portions over one-half hour. The mixture was heated at 75 degrees for 24 hours, with stirring during the first two hours. The reaction mixture was cooled, the solid mass shattered, and triturated in a mechanical blender with 300 ml of 2.4N hydrochloric acid. The solid was collected, washed with 3N hydrochloric acid, stirred in 400 ml of 0.5N sodium carbonate, and filtered. The filtrate, diluted with 250 ml of water, was gradually acidified with 4N hydrochloric acid. The precipitate was collected, washed with water, and dried to 38.5 g (79%) of the red title compound, mp 205-213 degrees. A purified sample, from toluene, melts at 212-215 degrees.

1-Chloro-7-methoxy-4-nitro-9(10H )-acridinone

A mixute of 12.9 g of 6-chloro-2[(4-methoxyphenyl)amino]-3-nitrobenzoic acid, 25 ml of chlorobenzene and 50 ml of phosphorus oxychloride was stirred and heated to reflux temperature over a period of one hour, and held under reflux for 4.5 hours. The mixture was cooled, filtered, and the filtrate concentrated to a viscous dark residue by evaporation under reduced pressure. The evaporation residue, and the precipitate collected previously were dissolved in 130 ml of acetic acid and cautiously treated with 15 ml of water, while stirring. The dark red title compound is collected, washed with water, and dried to 11.5 g (95%), mp 262-264 degrees.

EXAMPLE 13

1-Chloro-10-methyl-4-nitro-9(10H)-acridinone

A mixture of 8.24 g (0.03 mol) of 1-chloro-4-nitro(10H)-acridinone, 50 ml of DMF, and 1.8 g of a 57% dispersion of sodium hydride in mineral oil was stirred one-half hour at room temperature, and treated with 3.0 ml of methyl iodide. Stirring was continued for 17 hours, when 1.0 ml more of methyl iodide was added. At 22 hours, 0.1 g more of the sodium hydride dispersion was added, and at 24 hours, 1.0 ml more methyl iodide, and this mixture stirred 16 hours longer. The resulting dark red mixture was cooled to 0 degrees, the precipitate collected, washed with a little cold DMF, then with n-hexane, and teiturated in 200 ml of water. The aqueous suspension was filtered and the precipitate dried to 5.76 g (66%) of the title compound, mp 188-190 degrees.

In the same manner, 7.62 g (0.025 mol) of 1-chloro-7-methoxy-4-nitro-9(10H)-acridinone was converted to 5.05 g (63%) of 1-chloro-7-methoxy-10-methyl-4-nitro-9(10H)-acridinone, mp 235-240 degrees after recrystallization from toluene.

EXAMPLE 14

1,9-Dichloro-7-methoxy-4-nitroacridine

A stirred mixture of 12.9 g of 6-chloro-2[(4methoxyphenyl)amino]-3-nitrobenzoic acid, 25 ml of chlorobenzene and 50 ml of phosphorus oxychloride is heated to reflux temperature over a period of one hour, and held under reflux for 4.5 hours. The mixture is allowed to cool, the precipitate collected, providing the yellow title compound, mp 243-246 degrees after recrystallization from toluene.

EXAMPLE 15

1-Chloro-7-hydroxy-4-nitro-9(10H)-acridinone

Ten grams of 2-chloro-5-nitro-6-[[4-phenylmethoxy)-phenyl]amino]benzoic acid, 30 ml of 1,2-dichloroethane, and 30 ml of phosphorus oxychloride is stirred and heated to reflux over 10-15 minutes, and refluxed for 70 minutes. The resulting suspension is filtered, the precipitate washed with gl. acetic acid, then with acetone. The red solid is suspended in boiling toluene, collected, and dried, providing the title compound, mp above 325 degrees.

2-Chloro-5-nitro-6-[[4-(phenylmethoxy)phenyl]amino]-benzoic acid

A mixute of 50.0 g of 2,4-dichloro-3-nitrobenzoio acid, 85.7 g of 4-benzyloxyaniline, and 115 ml of N,N-dimethylaniline is heated on a steam bath for 24 hours. The cooled mixture is triturated with 600 ml of chloroform and filtered. The precipitate is stirred in a mixture of 350 ml of chloroform and 350 ml of 1N aq NaOH, the red sodium salt collected, and stirred with a mixture of 300 ml of 1N hydrochloric acid and 1.5 l of chloroform. The chloroform layer is concentrated, providing the title compound, red crystals, mp 172-174 degrees.

EXAMPLE 16

1-Chloro-4-nitro-7-(phenylmethoxy)-9-(10H)-acridinone

For grams of 2-chloro-5-nitro-6-]]4-phenylmothoxy)-phenyl]amino]benzoic acid is dissolved in 50 ml of hot chloroform, 0.2 ml of N,N-dimethylaniline is added, followed by 8.0 ml of phosphorus oxychloride. The mixture is stirred under reflux for 80 minutes. The resulting suspension is cooled in ice and the solid collected, providing the title compound, a red solid of mp 216-217 degrees.

EXAMPLE 17

N,N-Diethyl-7-methoxy-5-nitropyrazolo[3,4,5-kl]acridine-2(6H)-ethanamine, methanesulfonate (1:1)

A mixture of 1.52 g of 1-chloro-5-methoxy-4-nitro-9(10H)-acridinone and 1.50 g of [2-(diethylamino)ethyl]hydrazine in 15 ml each of THF and methanol was stirred at 50° for two hours, let stand at room temperature overnight, and evaporated to dryness. The residue, in chloroform, was washed with aqueous sodium bicarbonate, and chromatographed over 150 g of silica gel in chloroform, eluting with 2% methanolic chloroform, and evaporated to the title compound free base, mp 129°-131° C.

The title salt, mp 195°-198° C., crystallized from a methanolic ether solution of the base and an equivalent of methanesulfonic acid.

1-Chloro-5-methoxy-4-nitro-9(10H)-acridinone

A mixture of 23.6 g of 2,6-dichloro-3-nitrobenzoic acid, 100 ml of N,N-dimethylaniline, and 27.1 g of o-anisidine was held at 140° for 24 hours. The mixture was diluted with chloroform and extracted with 300 ml of N aqueous sodium hydroxide. Acidification of the extract caused precipitation of 6-chloro-2[(2-methoxyphenyl)amino]-3-nitrobenzoic acid.

A well-stirred mixture of 6.45 g of the above acid, 75 ml of chloroform, 0.5 ml of N,N-dimethylaniline, and 13.0 ml of phosphorus oxychloride was heated under reflux for 1.5 hour, and the precipitate recrystallized from chlorobenzene, providing the title compound, mp 315°-320° C.

EXAMPLE 18

N,N-Diethyl-9-ethoxy-5-nitropyrazolo[3,4,5-kl]acridine-2(6H)-ethanamine, methanesulfonate (1:1)

A suspension of 2.53 g of 1-chloro-7-ethoxy-4-nitro-9(10H)acridinone, 2.93 g of [2-(diethylamino)ethyl]hydrazine, and 150 ml of THF was stirred 18 hours at room temperature. The resulting solution was filtered, concentrated in vacuo to a solid, and washed with water. The dried solid was chromatographed over silica gel eluting with 1% methanol in chloroform. The desired fractions were combined and concentrated in vacuo to provide the free base of the title compound, mp 165°-167° C. A warm THF solution of the free base was treated with an equivalent of methanolic methanesulfonic acid to afford the title salt, mp 212°-214° C.

1-Chloro-7-ethoxy-4-nitro-9(10H)-acridinone

A mixture of 28.0 g of p-phenetidine, 23.6 g of 2,6-dichloro-3-nitrobenzoic acid, and 80 ml of N,N-dimethylaniline was heated five hours on a steam bath. The resulting mixture was diluted with chloroform and extracted with 1N sodium hydroxide. Acidification of the aqueous extract yielded 6-chloro-2-[(4-ethoxyphenyl)amino]-3-nitrobenzoic acid as reddish brown crystals.

Fifteen grams of the above acid together with 1.5 ml of N,N-methylaniline and 30 ml of phosphorus oxychloride in 200 ml of chloroform was stirred under reflux for two hours. After standing at room tempera overnight, the mixture was filtered, providing the title compound as shiny black crystals, mp 244°–246° C.

EXAMPLE 19

N,N-Diethyl-5-nitro-9-propoxypyrazolo[3,4,5-kl]acridine-2(6H)-ethanamine, methanesulfonate salt (1:1)

A slurry of 2.0 g of 1-chloro-4-nitro-7-propoxy-9(10H)acridinone in 175 ml of THF was stirred overnight with a solution of 1.6 g of [2-(diethylamino)ethyl]hydrazine in 30 ml of methanol at room temperature. Trituration in methanol of the residue from the concentration of the reaction mixture provided the free base, mp 141°–142° C. Treatment of a chloroform solution of this material with methanolic methanesulfonic acid provided the title salt, mp 209°–210° C.

1-Chloro-4-nitro-7-propoxy-9(10H)acridinone

A mixture of 24.5 g of 4-propoxyaniline, 19.8 g of 2,6-dichloro-3-nitrobenzoic acid, and 150 ml N,N-dimethylaniline was heated under nitrogen at 100° overnight. The cooled reaction mixture was treated with dilute base and chloroform. After the aqueous layer was washed several times with chloroform, it was treated with hydrochloric acid and the resulting orange needles were collected by filtration and washed with water to give 6-chloro-3-nitro-2-[(4-propoxyphenyl)amino]benzoic acid, mp 194°–196° C.

A mixture of 21.05 g of the above acid, 1 ml of N,N-dimethylaniline, 42 ml of phosphorus oxychloride, and 200 ml of 1,2-dichloroethane was heated at reflux 30 minutes. The reaction mixture was cooled to room temperature, and the resulting red solid was collected by filtration and washed with chloroform to provide the title compound, mp 174°–175° C.

EXAMPLE 20

9-Butoxy-N,N-diethyl-5-nitropyrazolo[3,4,5-kl]acridine-2(6H)-ethanamine, methanesulfonate A cooled (−10° C.) slurry of 2.5 g of 7-butoxy-1-chloro-4-nitro-9(10H)acridinone was treated with 1.84 g of [2-(diethylamino)ethyl]hydrazine and stirred at room temperature 18 hours. The reaction mixture was concentrated in vacuo to an oil, dissolved in chloroform, washed with dilute base, and dried. The crude material was chromatographed over silica gel eluting with 1% methanol in chloroform to provide the free base, mp 142.5°–143° C.

A solution of the free base in THF was treated with an equivalent of methanolic methanesulfonic acid to provide the title salt, mp 187°–189° C.

7-Butoxy-1-chloro-4-nitro-9(10H)acridinone

A solution of 25 g of p-butoxyaniline and 17.85 of 2,6-dichloro-3-nitrobenzoic in 50 ml of N,N-dimethylaniline was heated under nitrogen at 100° for 18 hours. The reaction mixture was treated with 500 ml of 0.2N sodium hydroxide and 500 ml of chloroform. The aqueous layer was washed with additional chloroform and acidified to provide 2-[(4-butoxyphenyl)amino]-6-chloro-3-nitrobenzoic acid, mp 166°–169° C.

A mixture of 17.9 of the above acid, 45 ml of phosphorus oxychloride, 3 ml of N,N-dimethylaniline, and 500 ml of chloroform was heated at reflux for two hours and then cooled in ice. The resulting red solid was collected by filtration and washed with cold chloroform to provide the title compound, mp 154°–155° C.

EXAMPLE 21

9-[2-(Diethylamino)ethoxy]-N,N-diethyl-5-nitropyrazolo[3,4,5-kl]acridine-2(6H)-ethanamine, methanesulfonate (1:2)

To a stirred solution of 1.95 g of 1-chloro-7-[2-(diethylamino)ethoxy]-4-nitro-9(10H)-acridinone in 40 ml of THF was added a 5 ml solution of 1.44 g of [2-(diethylamino)ethyl]hydrazine in THF over a period of 45 minutes. Methanol (10 ml) was added to dissolve the precipitate. The mixture was allowed to stand 24 hours, and evaporated to dryness. The residue was washed with water and chromatographed over 20 g of silica gel in chloroform, eluting with chloroform containing up to 10% methanol. The free base of the title compound, mp 137°–139° C., was converted to the title salt, mp 212°–214° C., in methanolic ethyl acetate containing two equivalents of methanesulfonic acid.

1-Chloro-7-[2-(diethylamino)ethoxy]-4-nitro-9(10H)acridinone

To a cold solution of 41.8 g of 4-nitrophenol in 250 ml of DMF was added 16.0 g of a 57% dispersion of sodium hydride in mineral oil, followed by 46.0 g of 2-diethylaminoethyl chloride. After 20 hours, the mixture was filtered, freed of solvent by evaporation under reduced pressure, the residue dissolved in ether and washed with water. Extraction with 2N hydrochloric acid and basification of the extract gave N,N-diethyl-2-(4-nitrophenoxy)ethanamine.

The above nitrobenzene derivative (26.2 g) in THF was hydrogenated over Raney nickel catalyst, the resulting mixture filtered and evaporated to 25.0 g of 4-[2-(diethylamino)ethoxy]benzenamine.

The above amine was added to a solution of 23.6 g of 2,6-chloro-3-nitrobenzoic acid in 60 ml of N,N-dimethylaniline, followed by 17.5 ml of N,N-diisopropylethylamine, and the resulting mixture heated at 60° for 25 hours under argon. Chloroform (300 ml) was added, and the orange precipitate of 6-chloro-2-[[4-[2-(diethylamino)ethoxy]phenyl]amino]-3-nitrobenzoic acid, mp 212°–215° C., collected.

A suspension of 18.3 g of the above carboxylic acid in 120 ml of 1,2-dichloroethane and 28.5 ml of N,N-dimethylaniline was treated with 5.0 ml of phosphorus oxychloride, stirred and heated 19 hours under argon, and filtered. The precipitate was shaken with chloroform and 100 ml of 0.5N aqueous sodium hydroxide, and the organic layer evaporated to provide the title compound, mp 148°–151° C.

EXAMPLE 22

N,N-Diethyl-9-[(4-methoxyphenyl)methoxy]-5-nitropyrazolo[3,4,5-kl]acridine-2(6H)-ethanamine, methanesulfonate (salt) (1:1)

To a suspension of 1.23 g of 1-chloro-7-[(4-methoxyphenyl)methoxy]-4-nitro-9(10H)-acridinone in 40 ml of THF and 5 ml of methanol was added a solution of 0.86 g of [2-(diethylamino)ethyl]hydrazine in 5 ml of THF over 40 minutes. The mixture was stirred 24 hours, evaporated to dryness, the residue washed with water, and chromatographed over 55 g of silica gel in chloroform, eluting with chloroform-methanol (50:1), providing the free base of the title compound, mp 156°–157° C.

The title salt, mp 182°–183° (dec) was prepared in methanol-ethyl acetate containing one equivalent of methanesulfonic acid.

1-Chloro-7-[(4-methoxyphenyl)methoxy]-4-nitro-9(10H)acridinone

To a solution of 24.2 g of sodium p-nitrophenoxide in 60 ml of DMF was added 23.5 g of 4-methoxybenzyl chloride. The precipitate was collected after 24 hours, washed with water, and recrystallized from chloroformcyclohexane, providing 1-methoxy-4-[(4-nitrophenoxy)methyl]benzene, mp 122°–124° C.

The above nitro compound was hydrogenated in THF-ethanol in the presence of Raney nickel catalyst, providing 4-[(4-methoxyphenyl)methoxy]benzenamine, mp 118°–120° C.

A mixture of 25 g of N,N-dimethylaniline, 9.23 g of N,N-diisopropylethylamine, 11.8 g of 2,6-dichloro-3-nitrobenzoic acid, and 11.5 g of 4-[(4-methoxyphenyl)methoxy]benzenamine was heated at 50°–80° C. for 135 hours and poured into 1200 ml of diethyl ether. The gummy precipitate was dissolved in chloroform and stirred with 100 ml of 1N aqueous sodium hydroxide. The red solid which formed was collected, suspended in 300 ml of water, 25 ml of 1N hydrochloric acid was added, and 6-chloro-2-[[4-[(4-methoxyphenyl)methoxy]phenyl]amino]-3-nitrobenzoic acid extracted with chloroform. Evaporation of the extract yielded red crystals, mp 173°–175° C.

A mixture of 8.15 g of the above carboxylic acid, 50 ml of 1,2-dichloroethane, 15.0 ml of N,N-dimethylaniline, and 2.15 of phosphorus oxychloride was allowed to stand at room temperature for 15 hours. The precipitate was collected, providing the title compound, mp 187°–189° C.

EXAMPLE 23

N,N-Diethyl-7,9-dimethoxy-5-nitropyrazolo[3,4,5-kl]acridine-2(6H)-ethanamine, methanesulfonate, hydrate (1:1)

A cooled (−20° C.) slurry of 2.5 g of 1-chloro-5,7-dimethoxy-4-nitro-9(10H)-acridinone in 150 ml of THF was treated with 1.98 g of [2-(diethylamino)ethyl]hydrazine in 50 ml of mathanol and stirred at room temperature overnight. After the reaction mixture was concentrated in vacuo, the residue was dissolved in chloroform, washed successively with dilute base and water, and dried. The concentrated solution was chromatographed over silica gel eluting with 2% methanol in chloroform to provide the free base of the title compound. The salt, mp 241°–242° C., was prepared by treating a chloroform solution of the free base with an equivalent of methanolic methanesulfonic acid, diluting with 2-propanol, and collecting the resulting orange solid by filtration.

1-Chloro-5,7-dimethoxy-4-nitro-9(10H)-acridinone

A mixture of 23.6 g of 2,6-dichloro-3-nitrobenzoic acid, 31.0 g of 2,4-dimethoxyaniline and 100 ml of N,N-dimethylaniline was heated for 24 hours on a steam bath, then for three hours at 150° C. The result was shaken with one liter each of chloroform and 4% ammonium hydroxide, and the layers separated. The aqueous layer was washed with chloroform, acidified, extracted with chloroform, the extract concentrated to 200 ml and diluted with cyclohexane. Dark red crystals of 6-chloro-2-[(2,4-dimethoxyphenyl)amino]-3-nitrobenzoic acid, mp 166°–170° C., were collected.

The above acid (7.36 g), 15 ml of phosphorus oxychloride, 1.0 ml of N,N-dimethylaniline and 125 ml of chloroform were combined and stirred under reflux for 1.5 hours, and let stand at room temperature overnight. The red precipitate of the title compound, mp 289°–293° C., was collected.

EXAMPLE 24

N,N-Diethyl-8,10-dimethoxy-5-nitropyrazolo[3,4,5-kl]acridine-2(6H)-ethanamine, methanesulfonate, hydrate (1:1:1)

A slurry of 2.0 g of 8-chloro-1,3-dimethoxy-5-nitro-9(10H)acridinone in 200 ml of cold THF was treated with 1.56 g of [2-(diethylamino)ethyl]hydrazine in 50 ml of methanol and stirred 18 hours. After the reaction mixture was concentrated in vacuo, the residue was dissolved in chloroform, washed with water and dilute base, and chromatographed over silica gel eluting with 2% methanol in chloroform to provide the free base, mp 213°–215° C. The salt was prepared by treating a chloroform solution of the free base with an equivalent of methanolic methanesulfonic acid to give an orange solid, mp 240°–241° C.

8-Chloro-1,3-dimethoxy-5-nitro-9(10H)acridinone

A mixture of 25 g of 2,5-dimethoxyaniline, 19.2 g of 2,6-dichloro-3-nitrobenzoic acid, and 60 ml of N,N-dimethylaniline was heated under nitrogen at 100° C. for 4d. The cooled reaction mixture was treated with 2N sodium hydroxide and dichloromethane. The aqueous layer was washed with dichloromethane several times and then acidified to provide 6-chloro-2-[(3,5-dimethoxyphenyl)amino]-3-nitrobenzoic acid, mp 174°–177° C.

A mixture of 17 g of the above acid, 40 ml of phosphorus oxychloride, 3 ml of N,N-dimethylaniline, and 600 ml of 1,2-dichloroethane was heated under reflux for two hours. After the reaction mixture was concentrated in vacuo, the resulting residue was treated with hot glacial acetic acid and diluted with water. The resulting solid was collected by filtration, and washed with water and methanol to provide the title compound, mp 291°–294° C.

EXAMPLE 25

10-Chloro-N,N-diethyl-9-methoxy-5-nitropyrazolo[3,4,5-kl]acridine-2(6H)ethanamine, methanesulfonate, hydrate A slurry of 0.85 g of 1,8-dichloro-2-methoxy-5-nitro-9(10H)acridinone in 100 ml of THF was treated with 1.4 g of [2-(diethylamino)ethyl]hydrazine and stirred one hour. After 2d of sitting in the cold, the solvent was removed in vacuo and the residue was triturated in methanol to provide the free base, mp 202°–204° C. Treatment of a chloroform solution of the base with ethanolic methanesulfonic acid provided the title salt, mp 271°–273° C.

1,6-Dichloro-7-methoxy-4-nitro-9(10H)acridinone and 1,8-dichloro-2-methoxy-5-nitro-9(10H)acridinone A mixture of 30 g of 3-chloro-4-methoxyaniline, 18.9 g of 2,6-dichloro-3-nitrobenzoic acid, and 150 ml N,N-dimethylaniline was heated at 100° under nitrogen for 24 hours. The reaction mixture was dissolved in chloroform and washed with dilute ammonium hydroxide. After the aqueous layer was washed with chloroform, it was acidified and the resulting orange solid was collected to provide 6-chloro-2[(3-chloro-4-methoxyphenyl)amino]-3-nitrobenzoic acid, mp 222°-228° C.

A mixture of 17 g of 6-chloro-2-(3-chloro-4-methoxyphenyl)amino]-3-nitrobenzoic acid, 35 ml of phosphorus oxychloride, 1 ml of N,N-dimethylaniline and 150 ml 1,2-dichlorcethane was heated under reflux for 45 minutes. The resulting solid was collected by filtration from the hot reaction mixture and was washed with chloroform to provide 1,6-dichloro-7-methoxy-4-nitro-9(10H)-acridinone, mp 284°-285 C.

From the cooled filtrate, another solid was obtained which was chromatographed over silica gel with dichloromethane to provide 1,8-dichloro-2-methoxy-5-nitro-9(10H)acridinone, mp 251°-253 C.

EXAMPLE 26

9-[[(1,1-Dimethylethyl)dimethylsilyl]oxy]-N,N-diethyl-5-nitropyrazolo[3,4,5-kl]acridine-2(6H)-ethanamine, methanesulfonate (salt) (1:1)

A suspension of 1.47 g of 2-2-(diethylamino)ethyl]-2,6-dihydro-5-nitropyrazolo3,4,5-kl]acridine-9-ol, 40 ml of dichloromethane, 1.05 g of tert-butyldimethylsilyl chloride, and 0.10 g of 4-dimethylaminopyridine was stirred at room temperature for 72 hours. The resulting dark yellow solution was diluted with 100 ml of dichloromethane, washed with water, concentrated, and chromatographed over 85 g of silica gel in chloroform, eluting with chloroform-methanol (50:1). The desired eluate was evaporated to give the free base of the title compound, mp 218°-220° C. The title salt was obtained from methanol-chloroform-ethyl acetate containing one equivalent of methanesulfonic acid, and recrystallized to mp 207°-213° C. from acetonitrile.

EXAMPLE 27

2-[2-(Diethylamino)ethyl]-2,6-dihydro-5-nitropyrazolo[3,4,5-kl]acridin-9-ol, acetate (ester), methanesulfonate (salt) (1:1)

A mixture of 1.10 g of 2-[2-(diethylamino)ethyl]-2,6-dihydro-5-nitropyrazolo[3,4,5-kl]acridin-9-ol, 40 ml of dichloromethane, 0.26 ml of acetyl chloride and 0.78 ml of N,N-diisopropylethylamine was stirred for 2.5 hours at room temperature. The mixture was evaporated to dryness, the residue triturated with ethanol, and chromatographed over 60 g of silica gel in chloroform, eluting with chloroform-methanol (50:1). The desired eluate was evaporated to dryness, and the residue combined with one equivalent of methanesulfonic acid in methanol-ethyl acetate. The resulting salt was recrystallized from methanolic acetonitrile providing the title compound, mp 250°-251° C., with decomposition.

EXAMPLE 28

2-[2-(Diethylamino)ethyl]-2,6-dihydro-5-nitropyrazolo[3,4,5-kl]acridin-9-ol, 2,2-dimethylpropanoate (ester), methanesulfonate (salt) (1:1)

A suspension of 1.84 g of 2-[2-(diethylamino)ethyl]-2,6-dihydro-5-nitropyrazolo[3,4,5-kl]acridin-9-ol, 60 ml of dichloromethane, 0.74 of trimethylacetyl chloride, and 1.31 ml of N,N-diisopropylethylamine was stirred at room temperature for 24 hours. One-half milliliter more of the acid chloride and 1.4 ml of diisopropylethylamine were added, and stirring was continued for 65 hours. The resulting dark yellow solution was diluted with 100 ml of dichloromethane, washed with water, and evaporated to a moist residue which was suspended in 40 ml of ethanol and filtered. The solid was recrystallized from 80 ml of acetonitrile, providing the free base of the title compound, mp 255°-258° C. (dec). The title salt, 233°-235° C. (dec), crystallized from a solution of the base in methanol-ethyl acetate-diethyl ether containing one equivalent of methanesulfonic acid.

EXAMPLE 29

[2-[2-(Diethylamino)ethyl]-2,6-dihydro-5-nitropyrazolo[3,4,5-kl]acridin-9-yl]butanoic ester, methanesulfonate (salt) (1:1)

A mixture of 1.47 g of 2-2-(diethylamino)ethyl]-2,6-dihydro-5-nitropyrazolo[3,4,5-kl]acridin-9-ol, 100 ml of 1,2-dichloroethane, 0.63 ml of butyryl chloride, and 1.74 ml of N,N-diisopropylethylamine was stirred at 50° C. for 2.5 hours, freed of solvent by evaporation under reduced pressure, and the residue triturated with water and collected. The crude product, in chloroform, was washed with 5% aqueous sodium bicarbonate, and chromatographed over 65 g of silica gel in chloroform. The desired eluate was evaporated to dryness and combined with methanesulfonic acid in methanolic ethyl acetate, providing the title compound, mp 220°-222° C.

EXAMPLE 30

Octanoic acid,[2-[2-(diethylamino)ethyl]-2,6-dihydro-5-nitropyrazolo[3,4,5-kl]acridin-9-yl]ester, methanesulfonate sulfonate (1:1), hemihydrate A mixture of 1.84 g of 2-[2-(diethylamino)ethyl]-2,6-dihydro-5-nitropyrazolo[3,4,5-kl]acridin-9-ol, 50 ml of 1,2-dichloroethane, 1.57 ml of N,N-diisopropylethylamine, and 1.20 ml of octanoyl chloride was stirred at 50° for two hours and evaporated to dryness. The residue was washed with water, dissolved in chloroform, and washed with 5% sodium bicarbonate. The solution was chromatographed over 100 g of silica gel in chloroform, and evaporated to a residue of the free base of the title compound, mp 136°-138° C.

The title salt, mp 159°-163° C., was obtained from methanol-ethyl acetate containing an equivalent amount of methanesulfonic acid.

EXAMPLE 31

2-2-(Diethylamino)ethyl]-2,6-dihydro-5-nitropyrazolo 3,4,5-kl]acridin-9-ol, benzoate (ester), methanesulfonate (1:1) (salt), monohydrate To a suspension of 1.84 g of 2-]2-(diethylamino) ethyl]-2,6-dihydro-5-nitropyrazolo[3,4,5-kl]acridin-9-ol in 50 ml of 1,2-dichloroethane was added 1.15 ml of benzoyl chloride, and 2.10 ml of N,N-diisopropylethylamine, and the mixture stirred five hours at 75° C. The resulting orange solution was evaporated to dryness, the residue washed with water, dissolved in chloroform and washed with aqueous sodium bicarbonate, and recrystallized from toluene-cyclohexane, providing the free base of the title compound, mp 192°-195° C. The title salt, mp 225°-228° C., crystallized from a solution of the base and one equivalent of methanesulfonic acid in methanolic ethyl acetate.

EXAMPLE 32

[2-[2-(Diethylamino)ethyl]-2,6-dihydro-5-nitropyrazolo[3,4,5-kl]acridin-9-yl]carbonic acid ethyl ester, methanesulfonate (salt) (1:1)

A mixture of 1.47 g of 2-[2-(diethylamino)ethyl]2,6-dihydro-5-nitropyrazolo[3,4,5-kl]acridin-9-ol, 50 ml of dichloromethane, 0.57 ml of ethyl chloroformate, and 1.05 ml of N,N-diisopropylethylamine was stirred 1.5 hours at room temperature, evaporated to dryness, the residue triturated with water, and chromatographed over 60 g of silica gel in chloroform. The desired portion of the eluate was evaporated to dryness, dissolved in ethyl acetate and treated with 3 ml of 1N methanolic methanesulfonic acid, causing precipitation of the title compound, mp 199°–201° C.

EXAMPLE 33

9-(Dimethylamino)-N,N-diethyl-5-nitropyrazolo[3,4,5-kl]acridine-2(6H)-ethanamine, methanesulfonate (1:2)

A suspension of 1.27 g of 1-chloro-7-(dimethylamino)-4-nitro-9(10H)-acridinone, 15 ml of THF and 15 ml of methanol, and 1.31 g of [2-(diethylamino)ethyl]hydrazine was stirred 24 hours at room temperature, cooled in ice and filtered. The solid was washed with cold methanol, then with water, dissolved in chloroform, washed with dilute aqueous ammonia, and chromatographed over silica gel, eluting with chloroform, and chloroform-methanol (50:1). The desired eluate was evaporated and crystallized from toluene-isooctane providing the free base of the title compound, mp 192°–196° C. The title salt, mp 206°–208° C., crystallized from a methanolic solution of the base and two equivalents of methanesulfonic acid upon addition of ethyl acetate.

1-Chloro-7-(dimethylamino)-4-nitro-9(10H)acridinone

A mixture of 41.0 g of N,N-dimethyl-p-phenylenediamine, 100 ml of N,N-dimethylaniline, and 23.6 g of 2,6-dichloro-3-nitrobenzoic acid was heated for seven hours on a steam bath. The resulting cake was suspended in dichloromethane, filtered, and the solid washed with water. Recrystallization from DMF-ethanol provided 6-chloro-2[[4-(dimethylamino)phenyl]amino]-3-nitrobenzoic acid, mp 222°–223° C. (dec).

To a solution of 8.40 g of the above acid in 300 ml of 1,2-dichloroethane and 19.0 ml of triethyl was added 4.2 ml of phosphorus oxychloride, the mixture stirred for two hours, and treated with 10.0 ml of methanol. This mixture was concentrated under reduced pressure to a residue which was triturated with 80 ml of methanol. The solid was collected, triturated with aqueous ammonia, dried, and recrystallized from DMF, providing the title compound, mp above 300° C., a black solid.

EXAMPLE 34

N,N-Diethyl-9-methyl-5-nitropyrazolo[3,4,5-kl]acridine-2(6H)-ethanamine, methanesulfonate (salt) (1:1)

A suspension of 1.44 g of 1-chloro-7-methyl-4-nitro-9(10H)-acridinone in 20 ml of methanol and 20 ml of. THF containing 1.44 g of [2-(diethylamino)ethyl]hydrazine was stirred at room temperature for 20 hours. The orange solid was recrystallized from toluene, providing the free base of the title compound, mp 213°–217° C.

The title salt, mp 204°–207° C., crystallized from a methanol-ether solution of the base and one equivalent of methanesulfonic acid.

1-Chloro-7-methyl-4-nitro-9(10H)-acridinone

A mixture of 10.7 g of p-toluidine, 11.8 g of 2,6-dichloro-3-nitrobenzoic acid and 25 ml of N,N-dimethylaniline was stirred at 135° for 160 minutes. The mixture was diluted with ether and extracted with 1N aqueous sodium hydroxide. Acidification of the aqueous solution, extraction with chloroform, and evaporation of the extract provided 6-chloro-2-[(4-methylphenyl)amino]-3-nitrobenzoic acid as orange prisms, mp 192°–197° C.

A solution of 10.2 g of the above carboxylic acid in 135 ml of chloroform containing 0.4 ml of N,N-dimethylaniline and 20.0 ml of phosphorus oxychloride was heated at reflux for three hours, cooled, and reddish-orange crystals of the title compound, mp 239°–241° C., were collected.

EXAMPLE 35

N,N--Diethyl-5-nitropyrazolo[3,4,5-kl]acridine-2(6H)-ethanamine, N-oxide, methanesulfonate salt (5:6), hydrate (4:3)

A solution of 1.5 g of N,N-diethyl-5-nitropyrazolo[3,4,5-kl]acridine-2(6H)-ethanamine in 50 ml of chloroform was treated with a solution of 1.1 g of 3-chloroperbenzoic acid in 50 ml of chloroform and stirred one hour at room temperature. The resulting solid, the 3-chlorobenzoate of the title compound, mp 143°–145° C., was collected by filtration and washed with chloroform. A methanolic solution of this material was adsorbed on basic alumina, and eluted with chloroform, and the fractions containing the desired free base were concentrated in vacuo to a gum. Treatment of a chloroform solution of this material with methanolic methanesulfonic acid provided the title salt, mp 173°–180° C.

EXAMPLE 36

N-Ethyl-9-methoxy-5-nitropyrazolo[3,4,5-kl]acridine-2(6H)-ethanamine, 1.25 methanesulfonate salt (4:5), hemihydrate A slurry of 1.43 g of 2-(2-chloroethyl)-2,6-dihydro-9-methoxy-5-nitropyrazolo[3,4,5-kl]acridine in 20 ml of ethylamine was heated in a pressure vessel 18 hours at 100°. After the excess ethylamine was removed in vacuo, the resulting solid was triturated in methanol to provide the free base, mp 168°–170° C. The title salt, mp 228°–230° C., was prepared by treating a chloroform solution of the base with methanolic methanesulfonic acid.

2-(2-Chloroethyl)-2,6-dihydro-9-methoxy-5-nitropyrazolo [3,4,5-kl]acridine

A solution of 3.6 g of 2-hydroxyethyl hydrazine in 5 ml of methanol and 20 ml of THF was added over 1.5 hours to a mixture of 6.09 g of 1-chloro-7-methoxy-4-nitro-9(10H)-acridinone in 75 ml of methanol and 55 ml of THF, and the resulting suspension was stirred 20 hours at room temperature. The precipitate was collected and recrystallized from DMSC-methanol, providing 9=methoxypyrazolo[3,4,5-kl]acridine-2(6H)ethanol, mp 275°–276 C.

A mixture of 6.0 g of the above alcohol, 7.0 g of 4-toluenesulfonyl chloride, 1.69 g of 4-dimethylaminopyridine, 5 ml triethylamine, and 100 ml of N,N-dimethylformamide was heated at 100° C. for 30 minutes and then diluted with a liter of water. The resulting solid was collected by filtration and then was triturated in methanol. Recrystallization in hot N,N-dimethylformamide provided the title compound, mp 264°–265° C.

EXAMPLE 37

9-Ethoxy-N,N-dimethyl-5-nitropyrazolo[3,4,5-kl]acridine-2(6H)ethanamine, methanesulfonate (4:5)

A slurry of 2.0 g of 1-chloro-7-ethoxy-4-nitro-9(10H)acridinone in 200 ml of cold (−10° C.) THF was treated with 1.42 g [2-(dimethylamino)ethyl]hydrazine in 20 ml of methanol and was stirred at room temperature two hours. After the solvents were removed under reduced pressure, the residue was chromatographed over silica gel eluting with 2% methanol in chloroform to obtain the free base, mp 195°–197° C. Treatment of a chloroform solution of the free base with methanolic methanesulfonic acid afforded the title salt, mp 214°–216° C.

EXAMPLE 38

7,9-Dimethoxy-N,N-dimethyl-5-nitropyrazolo[3,4,5-kl]acridine-2(6H)-ethanamine, methanesulfonate (1:1)

A slurry of 2.0 g of 1-chloro-5,7-dimethoxy-4-nitro-9(10H)-acridinone in 150 ml of cold (0° C.) THF was treated with 1.5 g of [2-(dimethylamino)ethyl]hydrazine in 50 ml of methanol and stirred at room temperature 3d.

The resulting solid was collected by filtration and washed thoroughly with methanol to provide the free base, mp 239°–241° C. Treatment of a chloroform solution of this material with methanolic methanesulfonic acid afforded the title salt, mp 260°–262° C.

EXAMPLE 39

9-(Dimethylamino)-N,N-dimethyl-5-nitropyrazolo[3,4,5-kl]acridine-2(6H)-ethanamine, methanesulfonate (1:2), dihydrate A mixture of 1.59 g of 1-chloro-7-(dimethylamino)4-nitro-9(10H)-acridinone, 20 ml of THF, 20 ml of methanol, and 1.35 g of [2-(dimethylamino)ethyl]hydrazine was stirred at room temperature for three hours, cooled in ice, and filtered. The precipitate was washed with cold methanol, then with water, and chromatographed over 50 g of silica gel, eluting with chloroform, and chloroform-methanol (50:1). The desired eluate was evaporated and converted to the title compound, mp 200°–206° C., by crystallization from methanol-ethyl acetate containing two equivalents of methanesulfonic acid.

EXAMPLE 40

2-[[2-(9-Ethoxy-5-nitropyrazolo[3,4,5-kl]acridin2(6H)-yl)ethyl]amino]ethanol, monohydrochloride, hydrate (4:1)

A slurry of 2.32 g of 1-chloro-7-ethoxy-4-nitro-9(10H)acridinone in 40 ml of THF was treated with 0.95 g of 2[(hydrazinoethyl)amino]ethanol in 50 ml of methanol and was stirred at room temperature 18 hours.

An orange solid was collected by filtration and was recrystallized in 25% methanolic DMF to provide the title salt, mp 283°–285° C. (dec).

EXAMPLE 41

2-[[2-(9-Butoxy-5-nitropyrazolo[3,4,5-kl]acridin-2(6H)yl)ethyl]amino]ethanol, methanesulfonate, hemihydrate A slurry of 2.0 g of 7-butoxy-1-chloro-4-nitro9(10H)acridinone in 100 ml of methanol was treated with 1.5 g of 2-[(hydrazinoethyl)amino]ethanol in 50 ml of methanol and stirred at room temperature 18 hours. The resulting free base, mp 170°–172° C., of the title salt was collected by filtration washing with methanol. By treating a chloroform solution of the free base with excess methanolic methanesulfonic adid, the title salt, mp 239°–241° C., was obtained.

EXAMPLE 42

2-[[2-(9-Methyl-5-nitropyrazolo[3,4,5-kl]acridin-2(6H)-yl)ethyl]amino]methanol, monohydrochloride A suspension of 1.44 g of 1-chloro-7-methyl-4-nitro-9(10H)-acridinone in 20 ml each of THF and methanol, and containing 0.71 g of [2-(hydrazinoethyl) aminoethanol, was stirred at room temperature for seven hours. The resulting suspension was filtered, the precipitate washed with THF, DMF, and acetone, in succession, providing the title compound, mp >300° C.

EXAMPLE 43

N,N-Diethyl-9-methoxy-5-nitropyrazolo[3,4,5-kl]acridine-2(6H)-propanamine, methanesulfonate, hydrate (1:1)

A slurry of 2.0 g of 1-chloro-7-methoxy-4-nitro-9(10H)acridinone in 150 ml of THF was treated with 2.09 g of 3-(diethylamino)propyl]hydrazine in 30 ml of methanol and was stirred two hours. After the solvents were removed in vacuo, the residue was crystallized in methanol to provide the free base, mp 143°–145° C. The title salt, mp 191°–193° C., was obtained by treating a chloroform solution of the base with methanolic methanesulfonic acid.

EXAMPLE 44

2-[3-(Dimethylamino)propyl]-2,6-dihydro-5-nitropyrazolo[3,4,5-kl]acridin-9-ol, methanesulfonate A suspension of 3.85 g of 1-chloro-7-hydroxy-4-nitro-9(10H)-acridinone in 50 ml of tetrahydrofuran and 50 ml of methanol containing 3.30 g of [3-(dimethylamino)-propyl]thylamino)propyl]hydrazine was stirred at 60° C. for 88 hours under argon. The orange precipitate was collected, dissolved in 120 ml of water at 80° C., and basified to pH 8–9 with aqueous sodium bicarbonate. The resulting suspension was filtered providing the free base of the title compound, mp 244°–247° C.

The title compound, mp 259°–261° C., was obtained by dissolving the base in aqueous methanol containing one equivalent of methanesulfonic acid and adding ethyl acetate.

EXAMPLE 45

9-Methoxy-N,N-dimethyl-5-nitropyrazolo[3,4,5-kl]acridine -2(6H)-propanamine, methanesulfonate A mixture of 2.13 g of 1-chloro-7-methoxy-4-nitro-9(10H)-acridinone and 1.8 g of [3-(dimethylamino)- propyl]hydrazine in 20 ml of methanol and 20 ml of THF was stirred at room temperature for 7.5 hours and evaporated to dryness. The residue was triturated with water and recrystallized from 30 ml of toluene and 20 ml of isooctane, providing the free base of the title compound, mp 176°–178° C.

The above base dissolved in 20 ml of aqueous methanol containing one equivalent of methanesulfonic acid, and upon addition of ethyl acetate, gave the title compound as orange crystals, mp 229°–232° C.

EXAMPLE 46

9-Ethoxy-N,N-dimethyl-5-nitropyrazolo[3,4,5-kl]acridine-2(6H)-propanamine, methanesulfonate (1:1)

A slurry of 2.0 g of 1-chloro-7-ethoxy-4-nitro-9(10H)acridinone in cold (−10° C.) THF was treated with 1.47 g of [3-(dimethylamino)propyl]hydrazine in 25 ml of methanol and was stirred at room temperature for three hours.

After the solvents were removed under reduced pressure, the material was chromatographed over silica gel eluting with 5% methanol in chloroform to provide the free base, mp 175°–176° C. Treating a chloroform solution of this material with an equivalent of methanolic methanesulfonic acid provided the title salt, mp 266°–268° C.

EXAMPLE 47

2-[3-(Dimethylamino)propyl]-5-nitropyrazolo[3,4,5-kl]acridin-9-ol, acetate (ester), methanesulfonate (salt) (1:1)

A mixture of 1.24 g of 2-[3-(dimethylamino)propyl]-2,6-dihydro-5-nitropyrazolo[3,4,5-kl]acridin-9-ol, 40 ml of 1,2-dichloroethane, 0.96 ml of acetyl chloride and 2.88 ml of N,N-diisopropylethylamine was stirred and heated at 80° under argon for three hours. The mixture was cooled, the orange solid was collected, and stirred with a mixture of chloroform-water with addition of sodium bicarbonate until the aqueous phase reached approximately pH 9. This mixture was filtered, the layers separated, and the chloroform solution evaporated providing an orange solid. This material, in 40 ml of ethyl acetate, was treated with 2.4 ml of 1N methanesulfonic acid, causing the title compound, mp 260°–264° C., to precipitate.

EXAMPLE 48

2-[3-(Dimethylamino)propyl]-5-nitropyrazolo[3,4,5-kl]-acridin-9-ol, 2,2-dimethylpropanoate (ester), methanesulfonate (salt) (1:1)

A mixture of 0.96 g of 2-[3-(dimethylamino)propyl]-2,6-dihydro-5-nitropyrazolo[3,4,5-kl]acridin-9-ol, 40 ml of 1,2-dichloroethane, 0.50 ml of trimethylacetyl chloride, and 0.97 ml of N,N-diisopropylethylamine was stirred under argon at 60° C. for 80 minutes. The resulting mixture was evaporated to dryness, dissolved in chloroform, washed with dilute sodium bicarbonate, and chromatographed over 75 g of silica gel, eluting with chloroform-methanol (50:1). The desired fraction was freed of solvents, dissolved in 40 ml of ethyl acetate and treated with 1.9 ml of 1N methanolic methanesulfonic acid causing the title compound, mp 243°–245° C., to precipitate.

EXAMPLE 49

2-[2-(Diethylamino)ethyl]-2,6-dihydro-3,5-dinitropyrazolo [3,4,5-kl]acridin-9-ol, methanesulfonate, hemihydrate A slurry of 0.9 of 1-chloro-7-hydroxy-2,4-dinitro-9(10H)-acridinone in 150 ml of 0° THF was treated dropwise over a one hour period with a mixture of 0.35 g [2-(diethylamino)ethyl]hydrazine and 0.36 g of N,N-diisopropylethylamine and then was stirred for two hours. After the solvent was removed in vacuo, the residue was triturated thoroughly with methanol to provide the free base, mp >290° C. The title salt, mp 249°–253° C., was prepared by treating a chloroform solution of the free base with methanolic methanesulfonic acid, collecting the resulting solid by filtration, and washing with ethanol.

1-Chloro-7-hydroxy-2,4-dinitro-9(10H)-acridinone

A mixture of 5.0 g of 2-chloro-6-[[4-[(4-methoxyphenyl)methoxy]phenyl]amino]-3,5-dinitrobenzoic acid, 10 ml of phosphorus oxychloride, 0.2 ml of N,N-dimethylaniline and 50 ml of 1,2-dichloroethane was heated at reflux for 15 minutes and the reaction mixture was filtered hot. The filter cake was washed with 1,2-dichloroethane to provide the title compound, mp 278°–281° C.

2-Chloro-6-[[4-[4-(methoxyphenyl)methoxy]phenyl]amino]-3,5-dinitrobenzoic acid

A solution of 12.65 g of 4-[(4-methoxyphenyl) methoxy]benzenamine in 150 ml of chloroform was added dropwise over 30 minutes to a solution of 15.7 g 2,6-dichloro-3,5-dinitrobenzoic acid and 15 ml of N,N-diisopropylethylamine in 250 ml of chloroform. After the reaction mixture was stirred at room temperature 18 hours, it was treated with dilute ammonium hydroxide. The resulting orange solid was collected by filtration, washed with water, and slurried in dilute hydrochloric acid to provide the title compound, mp 172°–174° C.

EXAMPLE 50

N,N-Diethyl-9-methoxy-3,5-dinitropyrazolo[3,4,5-kl]acridine-2(6H)-ethanamine, methanesulfonate (1:1), hydrate A slurry of 1.0 g of 1-chloro-7-methoxy-2,4-dinitro-9(10H)-acridinone in 150 ml of THF was treated with 0.76 g of [2-(diethylamino)ethyl]hydrazine and stirred at room temperature for two hours. After the solvent was removed in vacuo, the residue was dissolved in chloroform, washed with water, and chromatographed over silica gel with 1% methanol in chloroform to provide the free base, mp 243°–246° C. Treatment of a chloroform solution of the base with methanolic methanesulfonic acid provided the title salt, mp 277°–278° C.

1-Chloro-7-methoxy-2,4-dinitro-9(10H)-acridinone

A solution of 17.6 g of p-anisidine in 500 ml of chloroform was added over a 2.5 hour period to a 0° C. solution of 40 g of 2,6-dichloro-3,5-dinitrobenzoic acid and 47 ml of N,N-diisopropylethylamine in 800 ml of chloroform and then was stirred at room temperature overnight.

The reaction mixture was extracted with 6l of 5% ammonium hydroxide in 1l portions. After the aqueous layers were acidified with dilute hydrochloric acid, the resulting red solid was collected by filtration and washed with water to provide 2-chloro-6-[(4-methoxyphenyl)amino]-3,5-dinitrobenzoic acid, mp 241°-245° C.

A mixture of 21.5 g of the above acid, 43 ml of phosphorus oxychloride, 2 ml of N,N-dimethylaniline, and 100 ml of 1,2-dichloroethane was heated under reflux for 1 hour. After cooling, the resulting red solid was collected by filtration and washed thoroughly with 1,2-dichloroethane to provide the title compound, mp 253°-254° C.

EXAMPLE 51

9-Ethoxy-N,N-diethyl-3,5-dinitropyrazolo[3,4,5-kl]acridine-2(6H)-ethanamine, methanesulfonate, hydrate A cold slurry of 3 g of 1-chloro-7-ethoxy-2,4-dinitro-9(10H)-acridinone in 150 ml THF was treated dropwise with a solution of 1.15 g of [2-(diethylamino) ethyl]hydrazine and 1.1 g of N,N-diisopropylethylamine in 75 ml of THF over a two hour period. The reaction mixture was stirred for two hours in the cold and then allowed to stand in the cold 3d. After an insoluble gum was removed by filtration, the filtrate was concentrated in vacuo to a solid which was dissolved in chloroform and chromatographed over silica gel with 2% methanol in chloroform to obtain the free base. Treatment of a chloroform solution of the free base with methanolic methanesulfonic acid provided the title salt, mp 278°-280° C.

1-Chloro-7-ethoxy-2,4-dinitro-9(10H)-acridinone

A solution of 10.5 g of 4-ethoxyaniline in 250 ml acetonitrile was added over a 1.5 hour period to a solution of 20 g of 2,6-dichloro-3,5-dinitrobenzoic acid and 11 g of N,N-diisopropylethylamine in 400 ml of acetonitrile and stirred at room temperature for five hours. After the solvent was removed in vacuo, the residue was dissolved in 500 ml of chloroform and extracted with several portions of 5% ammonium hydroxide. The aqueous extracts were washed with chloroform and acidified with dilute acid. The resulting solid was collected by filtration and was washed with water to provide 2-chloro=6-[(4-ethoxyphenyl)amino]-3,5-dinitrobenzoic acid, mp 202°-206° C.

A mixture of 13.8 g of the above acid, 26 ml of phosphorus oxychloride, 1 ml of N,N-dimethylaniline and 200 ml of 1,2-dichloroethane was heated at reflux for one hour. After cooling slightly, the resulting reddish black plates were collected by filtration and washed with 1,2-dichloroethane to provide the title compound, mp 238°-241° C.

EXAMPLE 52

N,N-Diethyl-3,5-dinitro-9-(phenylmethoxy)pyrazolo [3,4,5-kl]-2(6H)-ethanamine, methanesulfonate, hemihydrate A slurry of 2.0 g of 1-chloro-7-(phenylmethoxy)-2,4-dinitro-9(10H)-acridinone in 150 ml of 0° C. THF was treated dropwise with a solution of 0.67 g of [2-(diethylamino)ethyl]hydrazine and 1.3 g of N,N-diisopropylethylamine in 50 ml over a one hour period and the mixture was stirred 18 hours at room temperature. After a small amount of solid was collected by filtration, the filtrate was reduced in vacuo to a solid which was triturated in methanol to provide the free base. The salt was prepared by treating the base with methanolic methanesulfonic acid and recrystallizing the resulting solid in aqueous ethanol to provide the title salt, mp 251°-253° C.

1-Chloro-2,4-dinitro-7-(phenylmethoxy)-9(10H)-acridinone

A mixture of 9.7 g of 2-chloro-3,5-dinitro-6-[[4-phenylmethoxy)phenyl]amino]benzoic acid, 200 ml of 1,2-dichloroethane, 20 ml of phosphorus oxychloride, and 1.0 ml of N,N-dimethylaniline was heated under reflux for 30 minutes. Upon cooling, a solid formed which was collected and washed with 1,2-dichloroethane providing the title compound, mp 217°-220° C.

2-Chloro-3,5-dinitro-6-[[4-(phenylmethoxy)phenyl]amino]benzoic acid

A slurry of 12.6 g of 4-benzyloxyaniline hydrochloride in water was treated with dilute sodium hydroxide and the resulting oil extracted into 600 ml of chloroform. The dried solution was added dropwise over a two hour period to a solution of 15 g of 2,6-dichloro-3,5-dinitrobenzoic acid and 6.9 g of N,N-diisopropylethylamine in 200 ml of acetonitrile, and the mixture stirred 24 hours. After the solvents were removed under reduced pressure, the residue was dissolved in chloroform and treated with dilute ammonium hydroxide. The gum which formed was collected, treated with hydrochloric acid, extracted back into chloroform, and then concentrated to provide the title compound, mp 208°-211° C.

EXAMPLE 53

N,N-Diethyl-9-[(4-methoxyphenyl)methoxy]-3,5-dinitropyrazolo[3,4,5-kl]acridine-2(6H)-ethanamine, methanesulfonate (1:1)

To a suspension of 1.71 g of 1-chloro-7-[(4-methoxyphenyl)methoxy]-2,4-dinitro-9(10H)-acridinone in 65 ml of THF, stirred and cooled in an ice bath, was added a 10 ml solution of 0.53 g of [2-(diethylamino)ethyl]hydrazine and 1.40 ml of N,N-diisopropylethylamine in THF over a period of two hours. The mixture was kept in ice for five hours longer and allowed to warm to room temperature over 15 hours. The mixture was evaporated to dryness, the residue was washed with water, dissolved in chloroform, and chromatographed over silica gel in chloroform providing the free base of the title compound, mp 204°-208° C.

The title salt, mp 218°-219° C. (dec), was obtained from methanolic-ethyl acetate containing an equivalent of methanesulfonic acid.

1-Chloro-7-[(4methoxyphenyl)methoxy]-2,4-dinitro-9(10H)-acridinone

To a stirred, ice-cold mixture of 2.67 g of 2-chloro-6-[[4-[(4-methoxyphenyl)methoxy]phenyl]amino]-3,5-dinitrobenzoic acid, 18 ml of 1,2-dichloroethane, and 4.4 ml of N,N-dimethylaniline, was added 0.70 ml of phosphorus oxychloride. After 2.5 hours, the ice bath was removed and the mixture stirred 24 hours at room temperature. The precipitate was collected, washed with water, then with methanol, and dried to provide the title compound, melting above 240° C. with decomposition

EXAMPLE 54

9-Methoxy-N,N-dimethyl-3,5-dinitropyrazolo[3,4,5-kl]acridine-2(6H)-ethanamine, methanesulfonate (1:1), hydrate A slurry of 2.0 g of 1-chloro-7-methoxy-2,4-dinitro-9(10H)-acridinone in 150 ml of −5° C. THF was treated with 1.5 g of 2-(dimethylamino)ethyl]hydrazine in 50 ml of methanol and stirred 18 hours. After the solvents were removed in vacuo, the residue was dissolved in chloroform and chromatographed over silica gel with 2% methanol in chloroform to provide the free base, mp 237°–239° C. Treatment of a chloroform solution of the base with methanolic methanesulfonic acid provided the title salt, mp 281°–282° C.

EXAMPLE 55

N,N-Dimethyl-3,5-dinitro-9-methoxypyrazolo[3,4,5-kl]acridine-2(6H)-propanamine, methanesulfonate (1:1)

A slurry of 2.0 g of 1-chloro-2,4-dichloro-7-methoxy-9(10H)acridinone in 200 ml of THF was treated with 0.68 g of [3-(dimethylamino)propyl]hydrazine and stirred three hours at room temperature. The resulting solid, the hydrochloride salt of the title compound, was collected by filtration and washed with THF. The salt was slurried in water, treated with dilute ammonium hydroxide and chloroform, and filtered to remove insoluble material. The chloroform solution was washed with water, dried over magnesium sulfate, treated with methanolic methanesulfonic acid, and diluted with acetone. The solution was concentrated in vacuo until a solid appeared. This solid was collected by filtration and recrystallized in aqueous methanol to provide the title salt, mp 267°–269° C.

EXAMPLE 56

N,N-Diethyl-9-methoxy-3,5-dinitropyrazolo[3,4,5-kl]acridine-1(6H)-ethanamine, methanesulfonate A slurry of 5.69 g of 1-chloro-7-methoxy-2,4-dinitro-9(10H)-acridinone in 400 ml of THF was treated with 4.32 g of [2-(diethylamino)ethyl]hydrazine and stirred 18 hours at room temperature. The resulting yellow solid, mp 191°–193° C., was collected by filtration and was washed with THF. This solid was stirred for two hours in a mixture of 400 ml methanol and 4 ml of methanesulfonic acid. Recrystallization of the resulting solid from aqueous methanol provided the title salt, mp 275°–278C.

PREPARATION OF INTRAVENOUS FORMULATIONS

EXAMPLE 57

A solution of 14.7 g of 2-[[2-[5-nitropyrazolo[3,4,5-kl]acridin-2(6H)-yl]ethyl]amino]methanol (from Example 3) as the hydrochloride salt is prepared in 1 liter of water for injection at room temperature with stirring. The solution is sterile filtered into 500 5-ml vials, each of which contains 2 ml of solution containing 25 mg of drug as the base, and sealed under nitrogen.

Alternatively, after sterile filtration into vials, the water may be removed by lyophilization, and the vials then sealed aseptically, to provide a powder which is redissolved prior to injection.

Having thus described my invention, what I claim and desire by Letters Patent to secure are the following:

1. A method for treating leukemia in a mammal which comprises administering a sufficient amount of a compound having the formula:

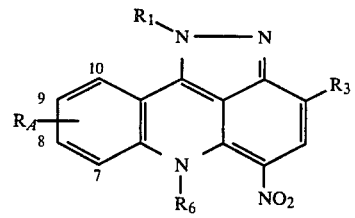

and the pharmaceutically acceptable salts thereof, where $R_1$ is -alkylene-$NR_xR_y$ where alkylene is two to four carbon straight or branched chain alkylene which can be substituted by hydroxyl, and $R_x$ and $R_y$ are each independently H, one to four carbon straight or branched chain alkyl, or two to four carbon straight or branched chain hydroxyalkyl, or combined with said nitrogen represent piperidyl or pyrrolidyl, when $R_x$ and $R_y$ are both alkyl, the amine may be an N-oxide; $R_3$ is H or $NO_2$; $R_6$ is H or one to three carbon straight or branched chain alkyl; $R_4$ is H or one or two groups selected from hydroxy, chloro, amino, one to four carbon straight or branched alkylamino or dialkylamino optionally substituted by methoxy, dimethylaminoethoxy, dimethylaminopropoxy, diethylaminoethoxy, diethylaminopropoxy, benzyloxy or benzyloxy substituted by methoxy, three to ten carbon straight or branched trialkylsilyoxy, two to twelve carbon straight or branched alkanoyloxy which may be substituted by methoxy, benzoyloxy or benzoyloxy substituted by methoxy, one to four carbon straight or branched alkoxycarbonyloxy, benzyloxycarbonyloxy, one to four carbon straight or branched alkylaminocarbonyloxy, benzyloxycarbonyloxy, one to four carbon straight or branched alkylaminocarbonyloxy or dialkylaminocarbonyloxy in combination with a pharmaceutically acceptable carrier, to a mammal in need thereof.

2. A method for treating leukemia a mammal which comprises administering a sufficient amount of a compound having the formula

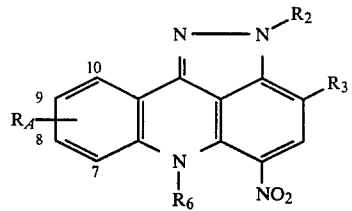

and the pharmaceutically acceptable salts thereof, where $R_2$ is -alkylene-$NR_xR_y$ where alkylene is two to four carbon straight or branched chain alkylene which can be substituted by hydroxyl, and $R_x$ and $R_y$ are each independently H, one to four carbon straight or branched chain alkyl, or two to four carbon straight or branched chain hydroxyalkyl or combined with said nitrogen represent piperidyl or pyrrolidyl, when $R_x$ and $R_y$ are both alkyl, the amine may be an N-oxide; $R_3$ is H or $NO_2$; $R_6$ is H or one to three carbon straight or branched chain alkyl; $R_4$ is H or one or two groups selected from hydroxy, chloro, amino, one to four carbon straight or branched alkylamino or dialkylamino optionally substituted by methoxy, dimethylaminoethoxy, dimethylaminopropoxy, diethylaminoethoxy, diethylaminopropoxy, benzyloxy or benzyloxy substituted by methoxy, three to ten carbon straight or branched trialkysilyoxy, two to twelve carbon straight or branched alkyanoyloxy which may be substituted by methoxy, benzoyloxy or benzoyloxy substituted by methoxy, one to four carbon straight or branched alkoxycarbonyloxy, benzyloxycarbonyloxy, one to four carbon straight or branched alkylaminocarbonyloxy or dialkylaminocarbonyloxy in combination with a pharmaceutically acceptable carrier, to a mammal in need thereof.

* * * * *